US012758374B2

(12) United States Patent
Chhaya et al.

(10) Patent No.: US 12,758,374 B2
(45) Date of Patent: Oct. 13, 2026

(54) 3D PRINTED IMPLANT WITH INTERNAL CHANNELS

(71) Applicant: BellaSeno GmbH, Leipzig (DE)

(72) Inventors: Mohit Prashant Chhaya, Leipzig (DE); Arpita Desai, Leipzig (DE); Navid Khani, Leipzig (DE); Sara Lucarotti, Leipzig (DE)

(73) Assignee: BellaSeno GmbH, Leipzig (DE)

( * ) Notice: Subject to any disclaimer, the term of this patent is extended or adjusted under 35 U.S.C. 154(b) by 81 days.

(21) Appl. No.: 18/800,265

(22) Filed: Aug. 12, 2024

(65) Prior Publication Data

US 2024/0398536 A1 Dec. 5, 2024

Related U.S. Application Data

(62) Division of application No. 17/251,529, filed as application No. PCT/EP2019/065264 on Jun. 12, 2019, now Pat. No. 12,083,007.

(30) Foreign Application Priority Data

Jun. 12, 2018 (EP) .................................... 18177214

(51) Int. Cl.
*A61F 2/00* (2006.01)
*A61F 2/12* (2006.01)
(Continued)

(52) U.S. Cl.
CPC .......... *A61F 2/0077* (2013.01); *B29C 64/386* (2017.08); *B33Y 50/00* (2014.12);
(Continued)

(58) Field of Classification Search
CPC ........ A61F 2/0059; A61F 2/0077; A61F 2/12; A61F 2002/0081; A61F 2210/0004;
(Continued)

(56) References Cited

U.S. PATENT DOCUMENTS 6,730,252 B1 5/2004 Teoh
2011/0125284 A1* 5/2011 Gabbrielli .............. B22F 7/004 623/18.11
(Continued)

FOREIGN PATENT DOCUMENTS

EP 2995278 A1 3/2016
JP 2008188132 8/2008
(Continued)

OTHER PUBLICATIONS

EPO Communication pursuant to Article 94(3) issued in App. No. EP19731646, dated Jul. 22, 2024, 8 pages.
(Continued)

*Primary Examiner* — Mohamed G Gabr
(74) *Attorney, Agent, or Firm* — Riverside Law LLP

(57) ABSTRACT

An implant for insertion into a patient is provided. The implant includes a three-dimensionally printed structure of layers. Each layer comprises an infill pattern of the three-dimensionally printed structure, the infill pattern of each layer comprising a set of infill lines. The implant includes a plurality of hollow channels. The layers are arranged on top of one another such that the plurality of hollow channels are formed within the implant, wherein the walls of each channel are formed by sections of the infill lines of a plurality of layers of the printed structure of layers. At least one hollow channel extends between a first outer surface of the implant and a second outer surface of the implant. At least one hollow channel is oriented in a direction which is tilted with respect to a reference axis perpendicular to the first outer surface of the implant.

16 Claims, 10 Drawing Sheets

(51) Int. Cl.
*B29C 64/386* (2017.01)
*B29L 31/00* (2006.01)
*B33Y 10/00* (2015.01)
*B33Y 50/00* (2015.01)
*B33Y 80/00* (2015.01)

(52) U.S. Cl.
CPC ....... *B33Y 80/00* (2014.12); *A61F 2002/0081* (2013.01); *A61F 2/12* (2013.01); *A61F 2210/0004* (2013.01); *A61F 2230/0019* (2013.01); *A61F 2240/002* (2013.01); *B29L 2031/7532* (2013.01); *B33Y 10/00* (2014.12)

(58) Field of Classification Search
CPC ...... A61F 2230/0019; A61F 2230/0021; A61F 2230/0086; A61F 2240/002; A61F 2250/0023; A61F 2250/0039; A61L 27/18; A61L 27/56; A61L 27/58; B29C 64/386; B33Y 10/00; B33Y 50/00; B33Y 80/00
See application file for complete search history.

(56) References Cited

U.S. PATENT DOCUMENTS

2012/0215310 A1* 8/2012 Sharp ........................ A61F 2/28 29/428
2014/0243995 A1 8/2014 Kolewe
2014/0255647 A1 9/2014 Johnson
2017/0258574 A1* 9/2017 Hutmacher ............. A61L 27/28

FOREIGN PATENT DOCUMENTS

JP 2017528225 9/2017
WO 02083194 10/2002
WO 2009097347 A1 8/2009
WO 2016038083 3/2016
WO 2018031491 A1 2/2018

OTHER PUBLICATIONS

Japanese Office Action (including English translation) issued in App. No. JP2021518991, dated Jul. 25, 2023, 9 pages.
Melchels Ferry P W et al, “Additive manufacturing of tissues and organs”, Progress in Polymer Science, (Dec. 8, 2011), vol. 37, No. 8, doi:10.1016/J.PROGPOLYMSCI.2011.11.007, ISSN 0079-6700, pp. 1079-1104, XP028927993.
Office Action (Non-Final Rejection) dated Feb. 1, 2024 for U.S. Appl. No. 17/251,529 (pp. 1-12).
Office Action (Notice of Allowance and Fees Due (PTOL-85)) dated May 13, 2024 for U.S. Appl. No. 17/251,529 (pp. 1-8).
Office Action (Notice of Allowance and Fees Due (PTOL-85)) dated Jul. 31, 2024 for U.S. Appl. No. 17/251,529 (pp. 1-2).

* cited by examiner

3D PRINTED IMPLANT WITH INTERNAL CHANNELS

CROSS-REFERENCE TO RELATED APPLICATIONS

This application is a divisional application of U.S. patent application Ser. No. 17/251,529, filed Dec. 11, 2020, which is the United States national stage patent application of International Application No. PCT/EP2019/065264, filed Jun. 12, 2019, which claims the right of priority from European patent application 18177214.6, filed with the European Patent Office on Jun. 12, 2018, which are hereby incorporated by reference in their entirety including all tables, figures, and claims for all purposes.

FIELD OF THE INVENTION

The present invention relates to the field of implants and, in particular, to a 3D (three-dimensional) printed implant with internal channels and the manufacture thereof.

BACKGROUND OF THE INVENTION

Nowadays, breast augmentation and breast regeneration surgery are one of the most common performed surgeries for aesthetic reasons. Since aesthetic aspects play an important role in breast surgery, one of the biggest concerns of women undergoing the surgery is the appearance of the final outcome. In fact, the aesthetic aspect is crucial also for the psychological condition of the patient, especially for women who experienced breast cancer and as a consequence thereof had portions of their natural breast tissue removed. Therefore, the attention to this field is increasing over time. Currently, even though different breast reconstruction or breast augmentation procedures are employed, both kinds of surgeries mostly rely on the insertion of silicone implants. Fat grafting is also a common technique and a combination of these two procedures can be used to improve the final outcome and, in particular, to fulfill the patient's aesthetic expectations.

However, despite their ubiquity in plastic surgery, silicone implants are known to sometimes have issues related to the appearance of the breast after surgery related to the unnatural look or big scars depending on the dimension of the inserted implant. Moreover, the main issue related to silicone implants is their limited life span. Since they are not lifetime products, the implant can burst inside the body after a certain period of time. A further complication due to an immune response of the body to the foreign implant material in the form of breast capsular contracture might occur which affects the stiffness of the breast, resulting in an unnatural tactile feeling. Even though non-surgical methods of treating capsules exist, the patient most often has to undergo a second surgery to remove or replace the implant.

To overcome the issues related to silicone implants and, in particular, to improve the safety for the patient, a new generation of bioabsorbable implants have been considered, which aim to support the regeneration of the tissue inside the body. Biodegradable materials, such as some thermoplastics, can be manufactured using a technique called injection moulding, where the melted material is injected in a mould, which gives the overall shape to the object. Unfortunately, this process shows limitations when complex detailed geometries need to be created. For example, in regenerative medicine, a high-porosity structure must be employed as template to facilitate tissue regeneration.

Recently, mainly due to the rapid developments in 3D printing technology, this technique has been considered for use in the manufacture of implants. A 3D printer typically creates a 3D object by an additive process. More popularly known as "3D printing", additive manufacturing (AM) is a canopy term for a group of technologies that build physical parts through extrusion of a material layer by layer, a process inherently different to classical machining which most commonly works via subtraction of a material block by drilling, milling etc.

The aforementioned breast implants can be manufactured using 3D printing, in particular fused deposition modelling (FDM) technology, and a biodegradable material such as polycaprolactone (PCL). This particular polymer may be advantageous because it is widely used in the medical field and is thus already approved by the regulatory bodies. Most importantly, PCL and meets the degradation requirement such that once it starts degrading, new tissue/vasculature can grow and settle inside the implant.

After the insertion of the implant manufactured by 3D printing, fat injection needs to be performed. Fat injection is necessary because the regenerated tissue which "regrows" in inside the implant has been observed to be stiffer than the natural breast tissue. Therefore, in order to make the final outcome as soft as natural breast tissue, a suitable percentage of fat is be collected, e.g. by means of liposuction, and injected into the implant using a specific needle. The injection procedure is problematic in the sense that random injections which perforate the structure several times can damage the filaments and affect the integrity of the overall structure of the implant. To overcome this issue, the procedure for designing the implant and the implant itself which facilitates fat injection disclosed in European patent application EP 2 995 278 A1 can be used. The procedure described in EP 2 995 278 A1 relates to the insertion of the implant to promote tissue regeneration inside the body and subsequent fat injection a certain period of time after the implantation. To avoid damages to the implant, a space for inserting the needle for fat injection should be provided. For this purpose, the implant disclosed in EP 2 995 278 A1 comprises a three-dimensional scaffold structure having voids which are filled with space-occupying structures that are removably attached to said three-dimensional scaffold structure. The space-occupying structures are provided to prevent invasion of tissue and/or of individual cells into said voids. After removal of the space-occupying structures in a second procedure, the resulting voids, which preferably may be interconnected and form one continuous channel structure, may be filled with fat or other transplantation cells.

However, the design of the corresponding 3D implant is rather challenging from the manufacturing point of view and not ideal from the patient's and surgeon's point of view. In fact, the channels formed after removing the space-occupying structures need to be considered during printing of the 3D implant and thus need to be included in the print instructions code which may lead to a weakened structure. Additionally, the subsequent removal of the space-occupying structures requires a further procedure and can bring about complications in that the freshly regrown tissue can be damaged, resulting in safety issues for the patient, and the injected fat can undergo necrosis or it can be reabsorbed if it is not well embedded in the structure due to a discrepancy between the predicted void space volume and the actual volume of the injected fat.

Thus, there is a need in the art for an improved implant which improves the final outcome and at the same time facilitates the overall procedure aiming to reconstruct lost tissue and/or restore tissue/organ function.

SUMMARY OF THE INVENTION

In various embodiments, the present invention relates to an implant comprising a three-dimensional structure of layers, each layer comprising an infill pattern; wherein the layers are arranged on top of one another such that a plurality of hollow channels are formed within the implant, wherein each hollow channel is oriented in a direction which is tilted with respect to the direction in which the layers are arranged on top of one another. The walls of each of the channels are formed by sections of infill patterns, in particular by filaments or bars of print material. Within the scope of this description, portions or segments of the thermoplastic feedstock extruded by the printer while manufacturing the infill pattern of a layer will be referred to as filaments.

The implant according to the present invention aims to overcome the above-described problems, in particular to facilitate the injection of biological material such as fat tissue into the implant and to remove the necessity of a second procedure during which voids for the injection the biological material are created. In the following, without loss of generality, only fat or fat cells/tissue will be referred to as a representative and highly relevant form of biological material which can be used for injection into the implant. However, it should be understood that any other type of cells or biological material may be injected into the implant, depending on its use.

The implant architecture of the present invention makes use of the channels which are naturally generated during manufacture of the implant and are thus already present in the machine instructions (e.g. G-code). In that manner, fat may be injected into the channels which are natively formed in the implant without damaging any filaments thereof. For this purpose, since the 3D printed implant presents a highly porous structure, the implant is designed such that the already existing channels extending through the implant coincide with the channels for fat injection. The channels of the implant according to various embodiments, which usually develop along the printing direction in conventional 3D printed objects, are oriented. Oriented channels do not have to lie in parallel with the printing direction. Preferably, as will be described later on, the channels may be additionally focused towards the area from where the surgeon may inject the fat into the implant. Therefore, the fat can be injected into the implant exploiting the natural structure of the implant, in particular the paths/channels formed therein, without damaging the implant itself. In particular, there is no need to provide additional or dedicated channels in the design of the implant and consequently the space-occupying structures known from EP 2 995 278 A1 need to be employed.

The term "implant", as used in the present application, relates to a medical device which is used to replace a missing biological structure, to support a damaged biological structure, and/or to enhance an existing biological structure. In particular, the implant of the present invention is an implant for the reconstruction of body tissue and/or the restoration of the function of a tissue or organ. Even though in the description the implant will be described as an implant for breast reconstruction or breast augmentation, the implant can be filled with any desired biological material and be employed at different sites of the body. Preferably, the implant may be printed from a biodegradable material. A suitable material for this purpose may be any thermoplastic and biocompatible or biodegradable material. For example, the material may include or consists of, but is not limited to, polycaprolactone (PCL), polygycolide, polylactide and/or a (co)-polymer of at least two or of those materials.

Various embodiments relate to an implant for insertion into a patient. The implant comprises a three-dimensionally (3D) printed structure of layers. Each layer comprises an infill pattern of the three-dimensionally printed structure. The infill pattern of each layer comprising a set of infill lines. The implant further comprises a plurality of hollow channels. The layers are arranged on top of one another such that the plurality of hollow channels are formed within the implant. The walls of each channel are formed by sections of the infill lines of a plurality of layers of the printed structure of layers. At least one hollow channel extends between a first outer surface of the implant and a second outer surface of the implant. At least one hollow channel is oriented in a direction which is tilted with respect to a reference axis perpendicular to the first outer surface of the implant.

In various embodiments, the first outer surface of the implant and the second outer surface are opposite-facing surfaces.

In various embodiments, the first outer surface is parallel to a two-dimensional plane formed by a first layer of the three-dimensional (3D) printed structure.

In various embodiments, the first outer surface is the largest planar surface of the implant.

In various embodiments, an angle between a longitudinal axis of a channel and the reference axis lies between 10 degrees and 85 degrees.

In various embodiments, the three-dimensionally (3D) printed structure of layers comprises a first batch of layers and a second batch of layers. The first batch of layers comprises odd-numbered layers of the three-dimensionally (3D) printed structure of layers, and the second batch of layers comprises even-numbered layers of the three-dimensionally (3D) printed structure of layers. The infill lines of the first batch of layers are oriented in a first direction, and the infill lines of the second batch of layers are oriented in a second direction different to the first direction. Portions of the infill pattern of the odd-numbered layer of the first batch of layers are shifted with respect to portions of the infill pattern of a first infill layer of the first batch of layers.

In various embodiments, portions of the infill pattern of the even-numbered layers of the second batch of layers are shifted with respect to portions of the infill pattern of a first infill layer of the second batch of layers.

In various embodiments, a lateral offset value between a first infill line of a first odd-numbered layer and a first infill line of a second odd-numbered layer lies between 0% and 50% of a distance between the first infill line of the first odd-numbered layer and a second adjacent infill line of the first odd-numbered layer.

In various embodiments, a lateral offset value between a first infill line of an $n+2*t$ odd-numbered layer and the first infill line of the first odd-numbered layer is smaller than the distance between the first infill line of the first odd-numbered layer and the second adjacent infill line of the first odd-numbered layer, for values of t smaller than or equal to 2.

In various embodiments, a lateral offset value between a first infill line of a first odd-numbered layer and a first infill line of a second odd-numbered layer lies between 50% and 100% of a distance between the first infill line of the first odd-numbered layer and a second adjacent infill line of the first odd-numbered layer.

In various embodiments, a lateral offset value between a first infill line of an n+2*t odd-numbered layer and the first infill line of the first odd-numbered layer is larger than the distance between the first infill line of the first odd-numbered layer and the second adjacent infill line of the first odd-numbered layer, for values of t larger than or equal to 2.

In various embodiments, the plurality of hollow channels converges towards a predefined region at the first outer surface or at the second outer surface of the implant.

In various embodiments, the predefined region is a point of a convergence located beyond the first outer surface or beyond the second outer surface of the implant.

In various embodiments, at least one hollow channel is a tapered channel.

In various embodiments, the tapered channels are configured such that the size of the openings of the channels on a bottom surface of the implant is in the range of 5-10 mm and the size of the openings of the channels on a top surface of the implant is in the range of 0.5-5 mm.

In various embodiments, more than two hollow channels of the plurality of hollow channels are tilted with respect to the reference axis by the same angle.

In various embodiments, at least 10% of the hollow channels of the plurality of hollow channels are tilted with respect to the reference axis by the same angle.

In various embodiments, at least one hollow channel of the plurality of hollow channels comprises a first opening at the first outer surface of the implant and a second opening at the second outer surface of the implant.

In various embodiments, at least one hollow channel of the plurality of hollow channels comprises a tilted portion and at least one non-tilted portion, wherein the non-tilted portion of the channel comprises one or more outer-most layers of the implant.

In various embodiments, the non-tilted portion of the implant is located between an opening of the channel at the first outer surface of the implant or at the second outer surface of the implant, and the tilted portion of the implant.

In various embodiments, the three-dimensionally (3D) printed structure of layers comprises a first batch of layers and a second batch of layers. The first batch of layers comprises odd-numbered layers of the three-dimensionally (3D) printed structure of layers. The second batch of layers comprises even-numbered layers of the three-dimensionally (3D) printed structure of layers. A first wall of a hollow channel is formed by sections of a plurality of odd-numbered layers of the first batch of layers. A second wall of the hollow channel is formed by sections of a plurality of even-numbered layers of the first batch of layers.

In various embodiments, a perimeter of each layer is determined by slices of a projected 3D model of the implant. The infill pattern of each layer is bound by the perimeter, such that when the layers are arranged on top of one another, the implant has a 3D form resembling the 3D model of the implant.

In various embodiments, the infill pattern of each layer comprises a print material meandering continuously from a start point of the layer to an end point of the layer.

Various embodiments relate to a method for forming an implant. The method comprises sequential printing layers to form a three-dimensionally (3D) printed structure, wherein each layer is printed according to an infill pattern, the infill pattern of each layer comprising a set of infill lines. The layers are printed on top of one another such that a plurality of hollow channels are formed within the implant. The walls of each channel are formed by sections of the infill lines of a plurality of layers of the printed structure of layers. Each hollow channel extends between a first outer surface of the implant and a second outer surface of the implant, wherein each hollow channel is oriented in a direction which is tilted with respect to a reference axis perpendicular to the first outer surface of the implant.

In various embodiments, the method further comprises providing a channel direction vector defining a tilt of the channels to be formed; specifying a pore dimension of a first pore of a layer to be formed at a first height, wherein the first pore is represented by a first line segment. The method further comprises specifying a pore dimension of a second pore of a layer to be formed at a second height, wherein the second pore is represented by a second line segment, the first pore and the second pore belonging to the same channel to be formed.

In various embodiments, the method further comprises determining a point of convergence of the channels to be formed by calculating a first orientation line by connecting left end points of a first line segment and a second line segment; calculating a second orientation line by connecting right end points of the first line segment and the second line segment, the direction vector lying on the second orientation line; and calculating an intersection of the first and second orientation lines to determine the point of convergence of the channels to be formed.

In various embodiments, the point of convergence lies outside the first outer surface or outside the second outer surface of the implant to be formed.

In various embodiments, the three-dimensional structure of interconnected layers which makes up the implant may be a scaffold structure which includes individual layers stacked upon one another. By gradually varying the shape of the layers stacked upon one another, the 3D implant may be given its desired form. The 3D scaffold structure of the implant may essentially comprise channels or pores arranged adjacent to one another and separated from one another by walls. The distance or a separation between adjacent channels may be the same from the bottom layers to the top layers of the channel. For example, the distance separating adjacent channels may be the thickness of the infill lines. A wall of a channel may comprise filaments (or portions thereof) of every other (alternating) layer. For example, a first wall of a channel may comprise filaments from first infill lines of odd-numbered layers. A second wall of the same channel may comprise filaments from second infill lines of odd-numbered layers. A third wall of the same channel may comprise filaments from first infill lines of even-numbered layers. A fourth wall of the same channel may comprise filaments from second lines of even-numbered layers. A first channel may be formed between the first infill lines of the odd-numbered layers and the second infill lines of the odd-numbered layers. A second adjacent channel may be between the second infill lines of the odd-numbered layers and third infill lines of the odd-numbered layers. In general, the infill pattern of the layers may be a design parameter and be configured in accordance with mechanical requirements of the implant, for example. According to various embodiments, the infill pattern of a layer n and of a layer n+2 may be similar in a sense that the infill patterns of those layers may include parallel bars/filaments (i.e. the portions of material). The infill layers of the implant may be configured such that the bars of a certain layer and the bars of a consecutive layer, depending on the individual design of the 3D implant, form an angle of less than 90°, (e.g. at least 10°, preferably of at least 30°, more preferably of at least 45°, more preferably of at least 60°, more preferably of) 90°. In other words, the bars of a certain layer may overlay the bars of a consecutive layer at a certain angle. The connection points between the bars of adjacent layers correspond to points of interconnection between the layers and provide structural integrity to the implant. In that manner, every layer is interconnected to its preceding and to its following layer.

The arrangement of the layers on top one another, wherein bars/portions of the infill pattern of a layer n are parallel to bars or portions of a layer n+2, is such that the bars are arranged above one another with an offset when viewed in the printing direction of the implant, i.e. in the direction in which the layers are stacked on one another. Such a configuration leads to the formation of pores or channels which are slanted and do not extend through the implant in parallel to the direction of printing. Therefore, each channel, starting at the bottom (surface) of the implant, i.e. the first layer that is printed, and ending on the top (surface) of the implant, i.e. the layer or portion thereof printed last at a given location on the surface of the implant, is oriented in a direction which is tilted with respect to the print direction.

According to various embodiments, the channel size may be constant, i.e. the cross-section of a channel at the level of any layer of the implant may be the same. In that case, the cross section of a channel corresponds to the geometrical shape of the opening of the channel at the bottom and to the opening of the channel at the top of the implant. In those embodiments, the tilt angle, i.e. the angle between the plane of the first printed layer and an axis extending through the channel in parallel to each of its walls, may be the same for each channel of the implant. In other words, each channel of the implant may be seen as a hollow channel forming a connection between an opening in the bottom surface and an opening in the top surface of the implant, wherein the channels do not run perpendicular to the bottom surface but are tilted in a certain direction.

According to various embodiments of the implant, substantially each of the hollow channels may comprise a corresponding first opening provided on a top surface of the implant, wherein each of the openings corresponds to an end of the channel. An opening of a channel does not necessarily have to lie in a plane which is parallel to the layers of the implant. An opening of a channel may be skewed in the sense that the outermost bars or strands of print material of a channel walls which define the opening of the channel may belong to different layers. As understood herein, a channel is considered hollow and open even if some filaments or strands of material run across its cross section. A channel which, when viewed from top or from bottom (i.e. along an axis running through the channel), is interspersed with filaments, is still considered hollow because single filaments extending between corners of the channel do not affect the capability of the channel to transport fat injected into the channel.

According to various embodiments of the implant, each of the hollow channels may extend between a first opening provided on a top surface of the implant and a second opening provided on a bottom surface of the implant. The bottom surface of the implant may correspond to the first layer printed during the manufacture of the implant. The top surface of the implant may be defined by layers or portions of layers (e.g. filaments) which only have one adjacent layer (in contrast to an inlying layer or portion of a layer which has two adjacent layers-one below and one above).

According to various embodiments of the implant, any of the walls of a hollow channel may be formed by a section of every other (alternate) layer (e.g. a bar of printed material) in the arrangement of layers forming the implant. The infill patterns of the layers may be designed such that any two adjacent layers of printed material form a crisscross pattern such that filaments or bars of the layers of printed material intersect at a certain angle, e.g. 90°. Therefore, a wall of a channel may include filaments or bars of every other layer, which, for example, may be parallel to one another. Due to the crisscross pattern of the filaments forming the 3D implant the filament of a layer lying between two layers which "contribute" filaments to a given wall is usually arranged at an angle with respect to the filaments of those two layers, e.g. at 90°, and therefore does not form part of that wall. A filament of a layer forming any of the walls of a given channel may be a straight line or a curved line of print material. It may be understood that the term infill lines, is not necessarily limited to being straight lines, but may also include curved lines, zig-zag lines and/or wiggled lines, for example.

According to various embodiments of the implant, at least one hollow channel may be a tapered channel. A tapered channel is characterized by a gradual increase or decrease of its cross section from the bottom opening to the top opening of the channel. In other words, the size (area) of the top opening and the bottom opening of a tapered channel are different, as the size of the channel varies along its orientation direction. According to various embodiments of the implant, the at least one tapered channel may converge towards a top surface of the implant. According to various alternative embodiments, the at least one tapered channel may diverge towards a top surface of the implant. Depending on the configuration of the tapered channel (converging or diverging), even though the amount of openings on the top surface and the bottom surface may be the same, the area of the bottom surface may be different from the area of the top surface sizewise. Advantageous embodiments of the implant may have multiple tapered channels, wherein the tapered channels may be convergent, divergent or of mixed kind. According to further embodiments, all channels of the implant may be tapered channels, preferably of the same kind (converging or diverging).

Embodiments of the implant with tapered channels may comprise bigger openings on the side of the implant facing the muscle, which is the highest source of blood vessels, wherein without loss of generality the size of the implant facing the muscle be referred to as the bottom side or bottom surface. Such a configuration of the implant according to the invention facilitates implant vascularization and the injection of fat. Channels which are focused to a specific area of the implant surface, for example to the anteroinferior side of the implant in the case of a breast implant, are easier to use for the surgeon, since the channels provide guidance with respect to the injection of fat into the implant. In particular, the direction of the channels in the implant may be chosen such that the fat may be injected from under the breast fold (inframammary injection). Furthermore, the implant is also more comfortable to use for the surgeon during the fat injection procedure, since the area from which the fat is injected is locally restricted to a specific area. Last but not least, the number of incisions and scars related to the procedure may be reduced by using, when applicable, the same inframammary incision for implant insertion and fat injection/grafting in order to reduce the number of scars.

Implants according to the present invention with different channel openings may be also used to specifically provide implants with heterogeneous mechanical properties in the printing direction, since areas with smaller channel openings tend to be stiffer than areas with bigger channel openings.

A particularly useful embodiment of the implant may be one where the channels are both tapered and slanted/tilted at the same time. In particular, in that embodiment all channels may be converging or diverging. Such a configuration of the channels of the implant allows "focusing" or orienting the top openings of the channels to a predefined area on the top surface of the implant.

According to various embodiments, the implant having tapered channels may be configured such that the size of the openings of the channels on the top surface of the implant (i.e. openings of the channels facing away from chest-wall in the case of a breast implant) may lie in the range of approximately 0.5-5 mm and the size of the openings of the channels on the bottom surface of the implant (i.e. openings of the channels facing the chest-wall in the case of a breast implant) may lie in the range of approximately 5-10 mm. In further embodiments, the size of the openings of the tapered channels on the bottom surface may lie in the range of approximately 6-9 mm and the size of the openings of the tapered channels on the top surface may lie in the range of approximately 1-4 mm. In yet further embodiments, the size of the openings of the tapered channels on the bottom surface may lie in the range of approximately 7-9 mm and the size of the openings of the tapered channels on the top surface may lie in the range of approximately 2-3 mm. In yet further embodiments, the size of the openings of the tapered channels on the bottom surface may lie in the range of approximately 8-9 mm and the size of the openings of the tapered channels on the top surface may lie in the range of approximately 3-4 mm. The specified sizes may relate to channels which have a quadratic cross-section.

The implant of the present invention offers several advantages over the implants known from prior art. First, since the "native" channels of the implant are used for injection and storage of fat and, in particular space-occupying structures are not needed, the implant according to the present invention can be manufactured using one material only. On the one hand, this reduces the risk of contamination between different materials. On the other hand, issues related to reduced bonding strength between strands/filaments of different material can be avoided since the end product may be manufactured from one single material. The use of one single material and thus one single infill/print pattern for the manufacture of the implant reduces the effort involved from the manufacturing point of view, because the resulting structure is easier to print using FDM technology. A further advantage, especially from the view of the patients, is that the overall surgical procedure is greatly facilitated since the necessity of a further procedure to remove structures from the implant to crate spaces for fat injection is removed. Consequently, trauma of tissue can be greatly reduced. The fact that nothing has to be removed from the implant after it has been inserted into the patient also provides for better biological performance, because the regenerated tissue will be left undisturbed such that the fat injected directly into the channels-which are naturally provided in the implant-will be well-embedded within the regenerated tissue. Last but not least, by tailoring the inner structure of the channels of the implant to the site of use, an optimal layout can be found in which the channels converge to a desired point or area on the surface of the implant, so that only one small incision is needed for both surgeries (implant insertion and fat injection).

Further embodiments of the invention will be now described in the following detailed description.

DETAILED DESCRIPTION OF THE INVENTION

Figure 1:
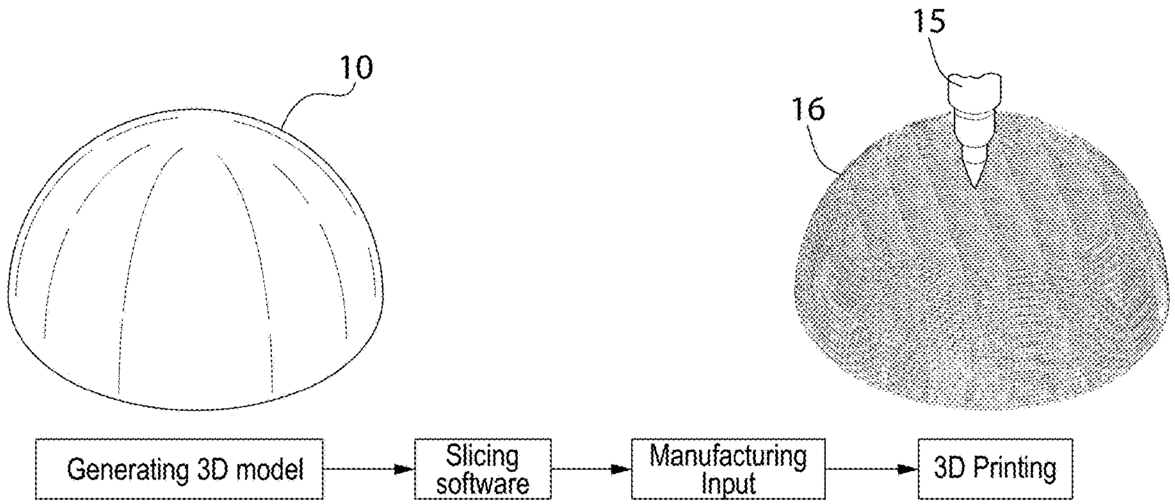
FIG. 1 illustrates steps performed during the manufacture of a 3D printed implant.

In FIG. 1, the core steps of a printing process of a 3D implant 16 are outlined. In a first step 11, a 3D model 10 of the implant 16 is designed using Computer Aided Design (CAD) software. At this stage, the 3D model 10 is primarily used to design the outer shape of the implant 16 according to need (e.g. adjusted to the size of an implant for a specific patient). In a second step 12, the designed 3D model is sliced into many layers using a infill software. The second step 12 may be seen as a transition from the theoretical continuous 3D model 10 into a layered definition of the continuous 3D model. The individual layers are so far undefined with regard to their inner structure, i.e. a potential infill pattern used for 3D printing of the layers. In a third step 13, manufacturing input is generated based on the layered 3D model. At this stage, an appropriate infill pattern is chosen for each layer of the 3D model 10. The manufacturing input comprises a set of machine instructions, readable by the 3D printer, by which the nozzle 15 of the 3D printer may be controlled in order to print the final implant 16 layer by layer. In a fourth and final step 14 a 3D "real-life" object in the form of the implant 16 is manufactured in accordance with the 3D model 10. The 3D implant 16 is manufactured by moving the nozzle 15 of the 3D printer in a coordinated motion, in accordance with the machine instructions, in all three Cartesian axes (X, Y and Z), laying down successive layers of a suitable print material on a surface until the object is fully built from bottom up. In general, the individual layers are manufactured in parallel to the XY-plane. The Z-axis is the vertical axis along which the nozzle 15 of the 3D printer is moved after finishing one layer in order to start extruding a subsequent layer. In the following, this definition of the three axes will be used in the following without loss of generality. The actions and three-dimensional movement pattern of the extruder and nozzle 15 which determine where the print material is extruded are controlled by a computer numerical control (CNC) programming language, typically G-code in consumer as well as in industrial 3D printers.

Figure 2:
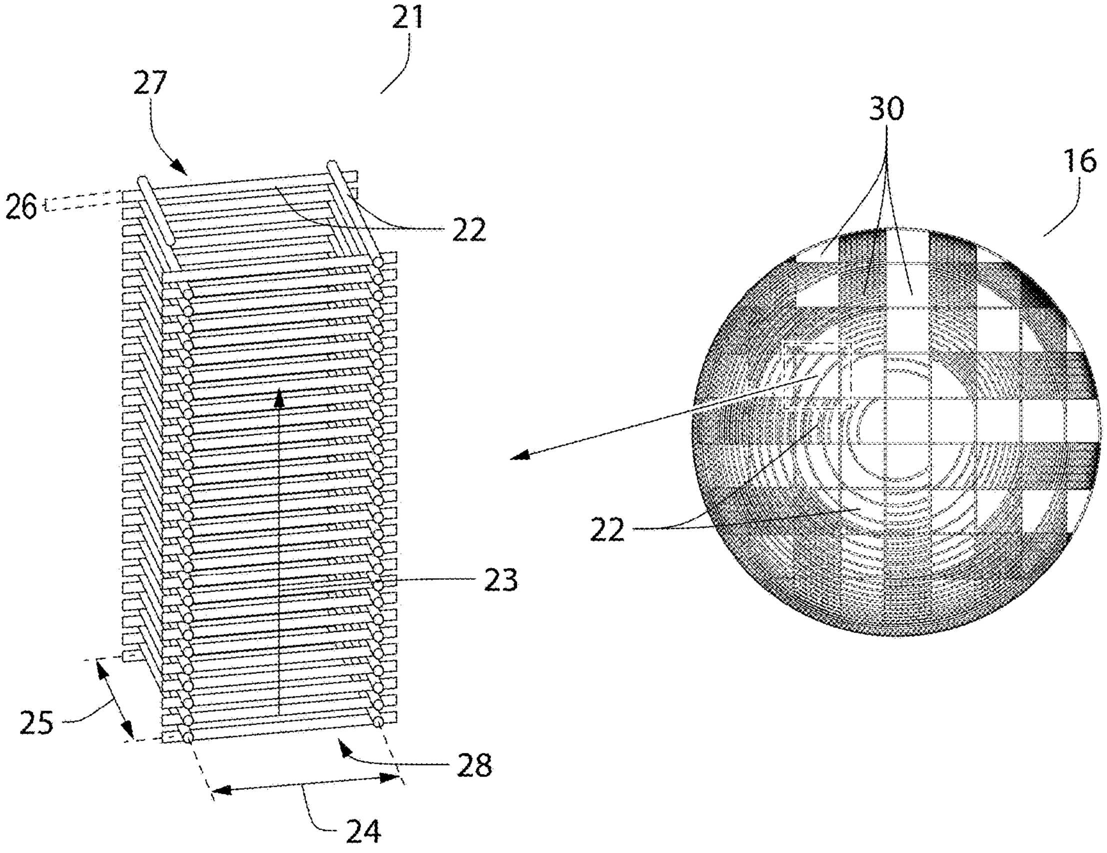
FIG. 2 shows a schematic top view of a 3D printed implant (right side) and an isolated view of a channel within the implant (left side).

In FIG. 2, a schematic top view of a 3D printed implant (right side) and an isolated view of a channel within the implant (left side) are shown. In the top view of the implant 16 on the right side of the figure it may be seen that the implant 16 comprises several channels 21 which extend vertically from the base of the implant 16. The channels 21 are arranged in a grid pattern. The channels 21 which are not located at the edge of the implant 16 have rectangular shapes. The channels which are located at the edge of the implant 16 may have different shapes, e.g. triangular shapes, since at least one of their walls is a wall which is used to model the desired outer shape of the implant 16. It is further shown that some channels 21 may have filaments or bars 22 of print material extending across their cross section. The filaments 22 which are shown to extend across cross sections of some of the channels 21 may, for example, be arranged in order to model the desired outer shape of the implant 16 or for reasons of mechanical stability.

A schematic channel 21 of the implant 16 (marked by a dashed circle) is shown on the left side of FIG. 2, wherein the arrow 30 indicates the extracted enlarged view of the channel 21. The channel 21 is formed by filaments or bars of print material 22 which are stacked on top of one another. In this example, the channel 21 has four walls, wherein at any level of the channel 21 a layer contributes two parallel bars 22 to two opposed walls, the bars 22 having a certain thickness 26 (which may vary throughout the implant 16). Optionally, the infill lines may have an average thickness of between 80 μm and 250 μm (or e.g. between 100 μm and 200 μm, or e.g. between 150 μm and 180 μm, e.g. 170 μm). The length 24 and width 25 of the channel 21 are given by the distances of a pair of adjacent bars 22 of the corresponding layers. However, it is not mandatory for the channels to have quadratic or rectangular shape, as the shape of the channels 21 may be arbitrary and, in particular, be defined by external parameters (e.g. stability and/or rigidity). The channel 21 further comprises a top opening 27 and a bottom opening 28. In this example of a uniform (untapered) channel 21, both openings 27, 28 are equal. Arrow 23 indicates the print direction which is parallel to the z-axis and perpendicular to the individual layers. Expressed differently, for implant designs with uniform channels 21 which are not slanted or tilted, the print direction coincides with the direction in which the layers are stacked on one another.

In 3D printing, the layers of printed material are stacked on top of one another. Therefore, the easiest and fastest way to create porosity is to print constant channels in the z-direction, i.e. channels having the same cross-section at any level (height) of the channel. Such configurations of implants have been shown in FIGS. 1 and 2. However, according to various embodiments of the implant provided herein, the architecture thereof is such that the channels of the implant are oriented towards a certain direction. This is explained in detail in FIG. 3 which shows different views of implants, with a perspective view shown in a first row 34, a top view shown in a second row 35 and a side view shown in a third row 36. In the left column, a projected form 31 of an implant 16 to be manufactured is shown, for example as planned in a CAD software. The projected form 31 may be designed under aesthetic aspects and primarily describe the outer form of the implant 16 to be manufactured. In the middle column, a conventional implant 32 with a form corresponding to the projected form 31 and having uniform channels 21 is shown. The channels 21 extend vertically from the bottom surface of the implant 16 towards its upper surface. The first arrow 37 which is shown in the perspective view 34 of the conventional implant 32 denotes the print direction. In the case of the conventional implant, however, the orientation of the channels 21 described by a second arrow 38 coincides with the print direction (therefore, the first arrow 37 corresponds to the second arrow 38 in the conventional design). That is, the first arrow 37 which represents a center axis of the channels 21 coincides with the second arrow 38. As can be seen from the top view 35, in the conventional implant 32 the top openings 27 overlay the bottom openings 28 of the channels 21.

In the right column, an implant 33 according to various embodiments is shown with a form corresponding to the projected form 31. As can be seen from the different views, the channels 21 extend from the bottom surface of the implant 33 to its top surface and are slanted/skewed. In other words, the orientation of the channels 21, denoted by the second arrow 38 does not coincide with the print direction which is denoted by the first arrow 37, such that the first arrow 37 representing print direction forms and angle with the second arrow 38 representing the orientation of the channels 21 with the angle being different from zero. The orientation of the channels may be chosen according to need, i.e. in accordance with a preferred site of fat injection and/or in accordance with mechanical requirements of the implant 16. As can be seen by comparing the side views 36 of the conventional implant 32 and the implant 33 according to various embodiments, the top openings 27 of the latter do not overlay the bottom openings 28 of the channels 21 when viewed from top in the direction corresponding to the print direction, i.e. the first arrow 37.

Figure 4:
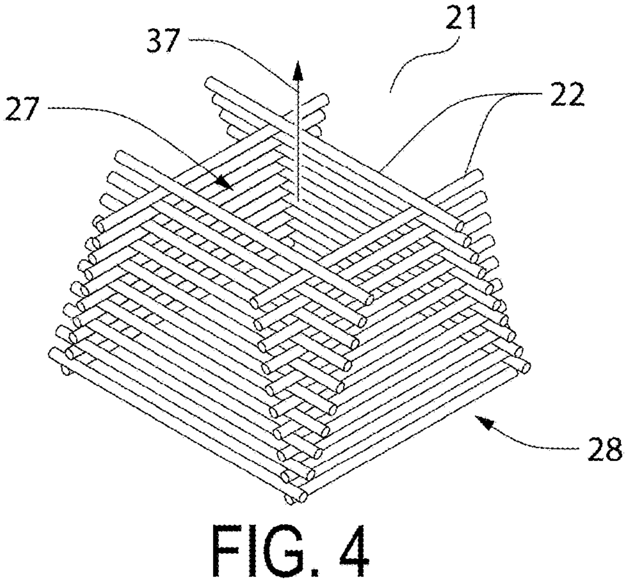
FIG. 4 illustrates a schematic view of an isolated tapered channel of an implant according to various embodiments.

In FIG. 4 the idea behind a further advantageous modification of the implant according to various embodiments is explained. FIG. 4 shows a setup of bars or filaments of print material 22 forming a channel 21 which is, in principle, similar to the channel 21 shown in FIG. 2. The channel 21 shown in FIG. 4, however, differs from the channel 21 shown in FIG. 2 in that it is a tapered channel which, in the shown exemplary embodiment, converges from its bottom opening 28 towards its top opening 27. Each of the four walls formed by every other bar 22 of a layer is slanted inwards, giving rise to the overall tapered form of the channel 21. As shown in FIG. 4, a converging channel, but also a diverging channel, may be characterized by a variation of its cross-section along the direction of the orientation of the channel 21 which is indicated by the first arrow 37. The orientation of a tapered channel may be defined as a line or axis which is interpolated from the middle points or center points of the cross sections of the channel 21.

Figure 3:
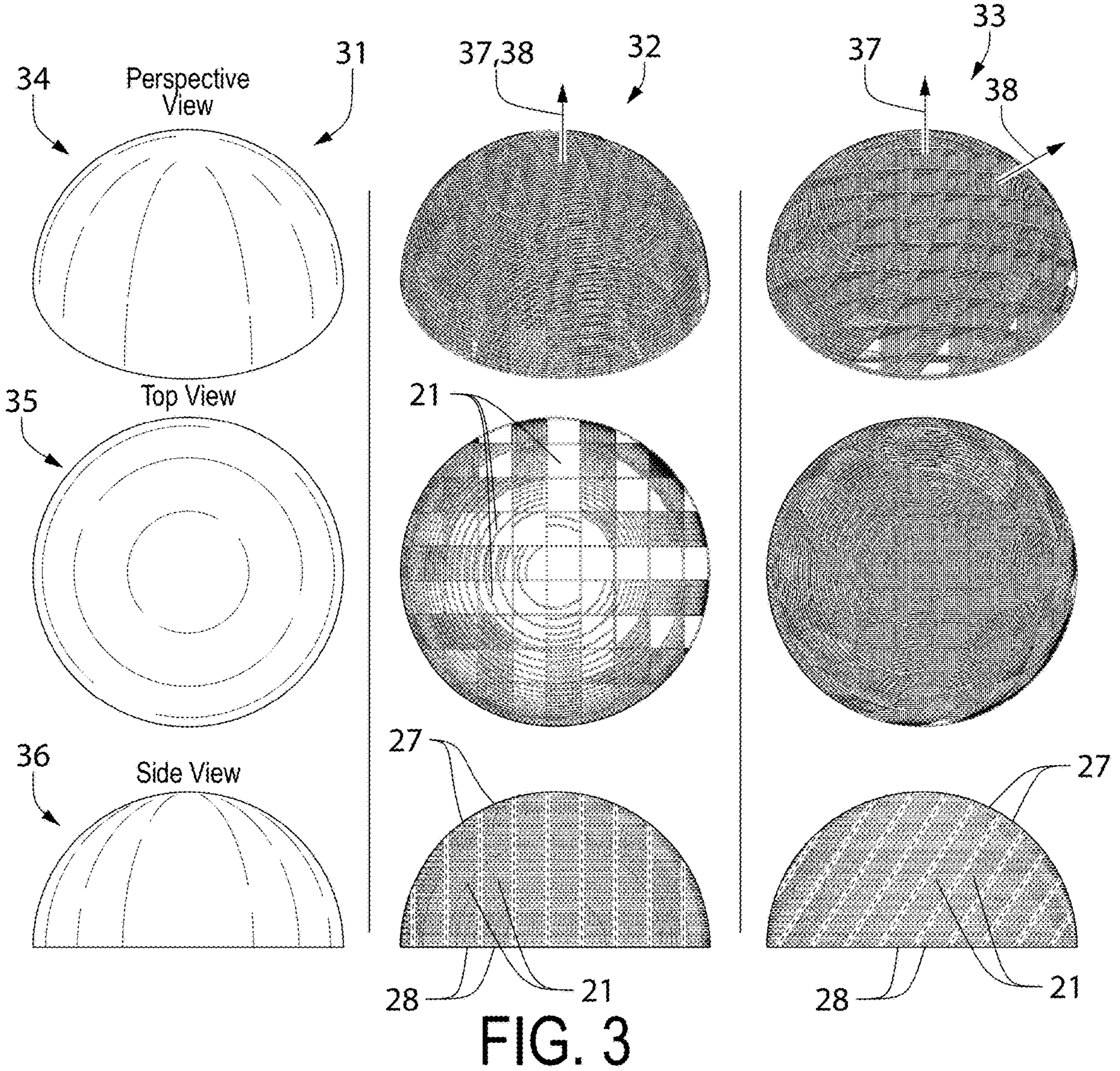
FIG. 3 shows various views of a general exemplary form of an implant (left column) and of an exemplary implant (middle column) and an implant according to various embodiments with different orientations of the internal channels (right column).
Figure 5:
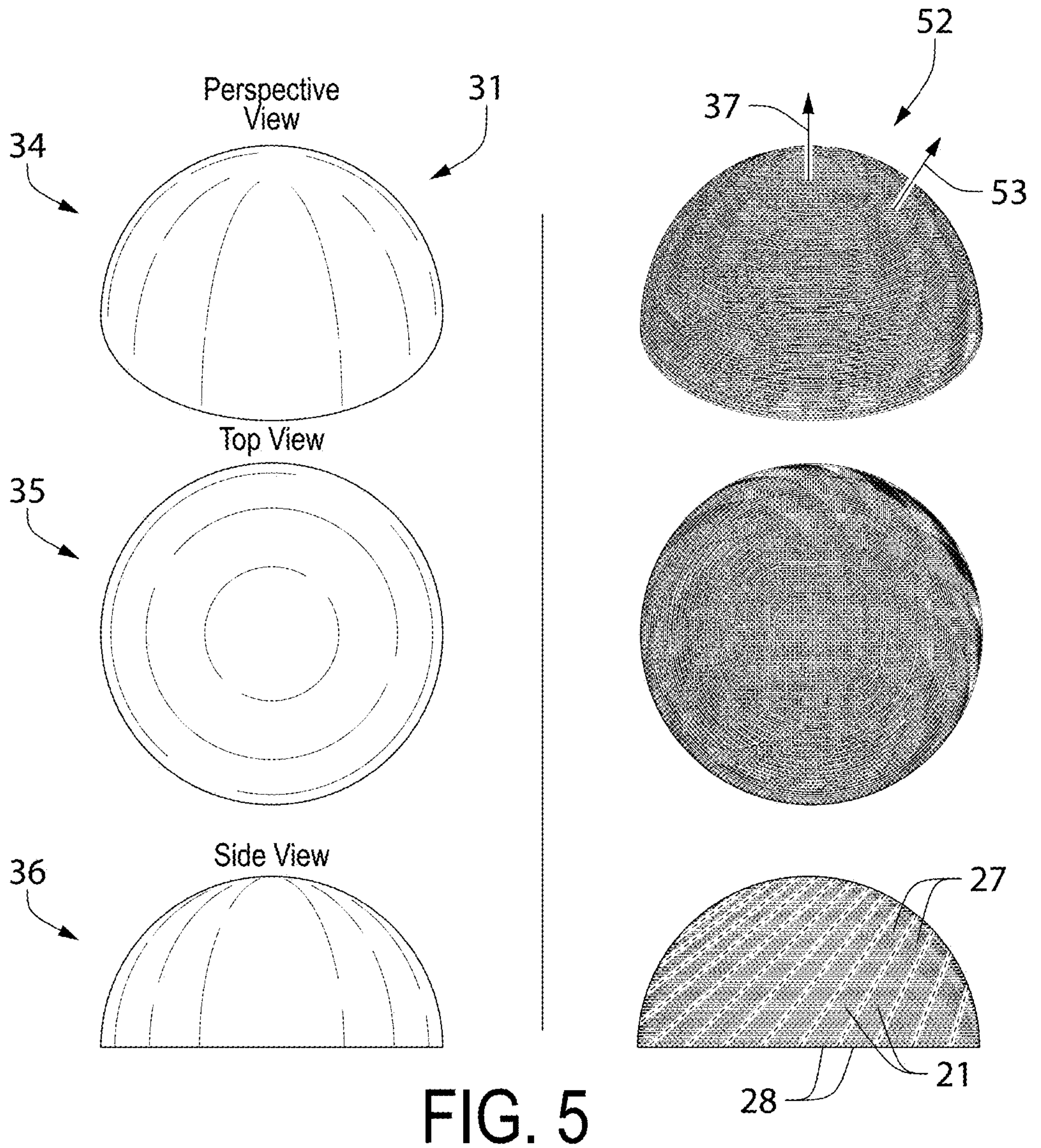
FIG. 5 shows different views of a general exemplary form of an implant (left column) and of an exemplary implant with tilted tapered channels according to various embodiments.

FIG. 5 shows a view of a projected 3D form 31 of an implant on the left side and the corresponding implant 52 according to various further embodiments on the right side. In analogy to FIG. 3, a perspective view is shown in a first row 34, a top view is shown in a second row 35 and a side view is shown in a third row 36. In the left column, the projected 3D form 31 of an implant to be manufactured from FIG. 3 is shown and taken as example again. The implant 52 is similar to the implant 33 of FIG. 3 in that its channels 21 are also tilted or oriented in a direction, which does not coincide with the print direction, represented by the first arrow 37.

In addition to the slant, the channels 21 are tapered, i.e. have a form which was already explained in detail based on FIG. 4. As can be seen from the different views depicting the configuration of the implant 52, the channels 21 extend from the bottom surface of the implant 33 to its top surface and their top openings 27 are focused towards a predefined region of the top surface of the implant 52 (in this exemplary scenario: upper right corner). The third arrow 53 denotes the focus direction and may correspond to an axis defined by two points: the middle of the bottom surface/layer of the implant 52 and the point of intersection of all orientation axes of the individual channels 21. Instead of the bottom surface/layer, the first point may also correspond to the projection of the center of mass of the implant 52 on the base, i.e. the bottom surface/layer, of the implant 52. Alternatively, or optionally, the first point may be any point within the bulk volume of the implant. Depending on the desired design, the third arrow 53 may practically point to any direction.

As already described above, the exemplary embodiment of the implant 52 shown in FIG. 4 with oriented pores/channels, which converge towards a predefined region or direction on the upper surface of the implant 52, facilitates the fat injection procedure for the surgeon and allows the patient to have only one scar on the breast. The reason for this is that in one of the most commonly used methods to insert an implant relies on an infra-mammary incision. Since fat injection will be performed after a couple of weeks after the implant insertion, with the implant according to various embodiments the incision used for the insertion can be advantageously also used for fat injection. The pattern of oriented channels 21 can be then used as a guide for the surgeon during injection of the fat. Since the needle will be aligned with the channels 21, the implant will not be damaged by the needle itself.

Oriented pores/channels in an implant which is a printed porous structure may be further advantageously used to reduce the stiffness of the overall structure in the printing direction. The angle of orientation or the angle of convergence, i.e. the angle between the xy-plane (plane of printing) and the orientation direction or the focus direction, respectively, makes that stiffness tunable. In general, the smaller the angle of convergence, the softer the structure. This concept is further exemplified in FIG. 6 which shows a first implant 61 having tapered channels and a second implant 62 having uniform channels, both having slanted channels. As in the previous cases, the first arrow 37 denotes the printing direction for both exemplary implants 61, 62 and the third arrows 53 displayed on the first implant 61 indicate the direction of focus of the individual channels. As can be deduced from the orientation of the third arrows 53, the channels are focused towards the top center of the implant 61. In the second implant 62, the third channels 53 are oriented towards the right side of the implant 62. Since the angle of convergence of the second implant 61 is a lot smaller than the angle of convergence of the second channel (which is close to) 90°, the lateral shift from one layer to the next and consequently the lateral shift from one filament to the next is larger in the second implant 62. Thus, the filaments in the second implant 62 are not arranged directly on top of each other. This macroscopic effect leads to a softer second implant 62 as compared to the first implant 61.

Figure 7:
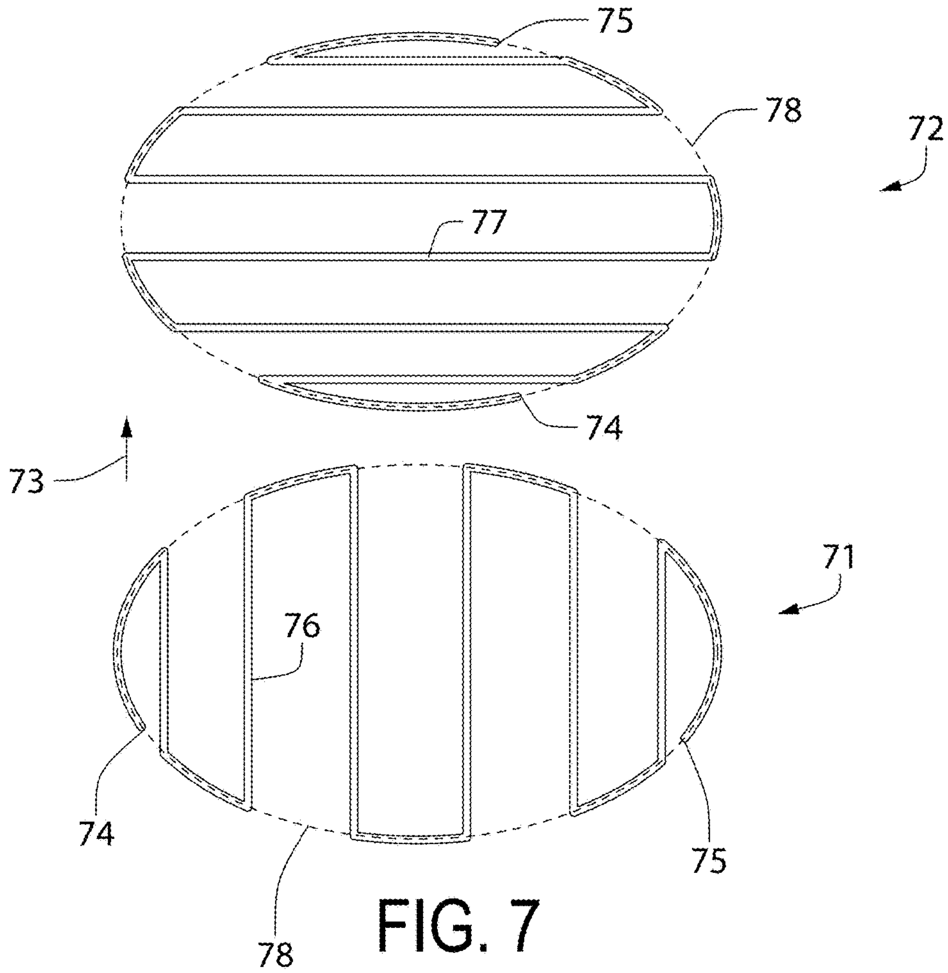
FIG. 7 shows two exemplary layers of an implant according to various embodiments manufactured by 3D printing.

As already outlined above, the implant according to various embodiments is manufactured by sequential printing of the layers. In FIG. 7, an exemplary first layer 71 and an exemplary second layer 72 are shown. During manufacturing of the layers 71, 72 by 3D printing, each layer is printed in the form of a line of print material between starting point 74 and an end point 75 according to a predefined infill pattern 76, 77. As shown, the first 71 comprises a first infill pattern 76 and the second layer 72 comprise a second infill pattern 77, both infill patterns 76, 77 having a zigzag shape. The starting points 74 and end points 75 are not necessarily visible in the final product and have been exaggerated in the schematic view shown in FIG. 7 for ease of understanding. The perimeter 78 of each of the layers 71, 72 is determined by the slices of the projected 3D model of the implant. That is, each infill pattern 76 is bound by the perimeter 78 such that when the layers manufactured during the printing process are stacked on top of one another, the final 3D product has a 3D form that closely resembles the projected 3D model.

Portions of the infill pattern located at the perimeter 78 of a corresponding layer are printed such that they trace the perimeter 78. The inside of the layers 71, 72 may be filled with an infill pattern of any shape which may be chosen according to boundary conditions (stiffness, porosity, density). After the 3D printer has extruded the infill pattern of the first layer 71, the nozzle is halted at the end point 75 of the first layer 71, the distance between the nozzle and the plane of printing is altered (usually by moving the nozzle upwards in the direction indicated by the arrow 73) and the infill layer of the second layer 72 is formed, starting at the starting point 74 of the second layer 72.

After the second layer 72 has been printed on top of the first layer 71, a third layer is deposited on the second layer. The third layer (not shown in FIG. 7) may resemble the first layer. As shown in FIG. 7, the lines of material of the first infill pattern 76 which are not arranged on the perimeter 78 of the first layer 71 are arranged at an angle to the lines of material of the second infill pattern 77 which are not arranged on the perimeter 78 of the second layer. This arrangement gives rises to the channels within the final implant. Oriented channels and/or slanted channels are formed by gradually shifting the inner structure of the infill patterns 76, 77 in the desired direction. For example, a channel oriented to the right side of FIG. 7 can be formed by manufacturing the first layer 71 as shown in FIG. 7 and then shifting the straight bars of the infill layer of the third layer to the right with respect to the first infill layer 76, such that when looked at from the top from the perspective shown in FIG. 7., the straight bars of the infill pattern of the third layer are offset to the right with respect to the straight bars of the first infill pattern. Continuing the process for the other odd numbered layers leads to an implant as shown in the right column of FIG. 3. Tapered channels can be formed by arranging the lines of print material of the infill patterns as shown in FIG. 4.

Further provided herein is a method for generating a printing path of a 3D printer for printing a porous object comprising channels extending through the porous object, such as the 3D implant described herein. The channels of the porous object are formed by pores comprised by layers printed during the manufacture of the porous object. The generated printing path comprises a set of path points along which the printing nozzle of the 3D printer is moved in order to print the layers of material, one by one, to ultimately manufacture the 3D implant.

In a first step, the method for generating a printing path according to various embodiments comprises decomposing the 3D model of the porous object (3D object) into a set of layers, each layer comprising a contour of the 3D model at a corresponding height of the 3D model, the height being aligned with the print direction. The first step may thus include infill of the 3D model into slices, each slice representing a printing layer. During printing, each layer is manufactured by extruding print material from the printer's nozzle along a printing path. Usually, the individual planes are parallel to the print surface on which the 3D object is printed which is assumed to correspond to the xy-plane. The layers are manufactured by extruding print material on top of each other in the print direction which is assumed to correspond to the z-direction. The overall extrusion of the layers generally takes place in a crisscross pattern, such that filaments of one layer are extruded on the filaments of the previous layer at a certain angle, most commonly 90°. The aim of this first step of the method which corresponds to the design/planning phase is the generation of layers, each layer containing the contour of the 3D model at a corresponding height of the 3D model. The structure of the inside of each layer is a design parameter and may be chosen later on according to needs of the respective application.

In a further step the method includes intersecting one or more layers in the set of layers with a set of infill lines, wherein the distance between the infill lines for each layer is set to correspond to the dimension of the pores in that layer in a direction perpendicular to the infill lines. By intersecting a layer with a set of infill lines, the layer is segmented into stripes, with two opposing sides simply corresponding to portions of two adjacent infill lines and the other two opposing sides representing portions of the contour of the layer. The infill lines preferably correspond to representations of portions of material which are extruded during the printing process. The two opposing sides representing portions of the contour of the layer may be approximated by straight lines during the printing process, wherein the straight lines extend between the corresponding edges of the stripe. In some embodiments, the infill lines may be equidistant, thus leading to homogenously sized pores within the layer.

In a further step of the method, the printing path is formed for the one or more layers (which has been "sliced" in the previous step) on the basis of the intersections between the set of infill lines and the contour of the corresponding layer. In that sense, the infill lines may be also referred to as searching lines as they are used to search for the intersections thereof with the contour of the layer. Preferably, the printing path of a given layer may consist of the intersections arranged in such an order that, during printing of the 3D object, the nozzle will be moved along the printing path in a meandering manner, from one intersection to the next, and extrude print material continuously from a start point to an end point of the layer. It is noted that while a respective layer substantially comprises the contour and the calculated intersections all lie on the contour of the layer, the material layer of the 3D object which is extruded on the basis of the calculated intersections may comprise an intermittent representation of the contour of the layer and an infill comprising straight lines of print material (which correspond to infill lines), as shown in FIG. 7, for example. However, in contrast to the layer shown in FIG. 7, the portions of the intermittent representation of the contour of the layer may be also approximated by straight lines instead of curvy or arcuate lines in order to simplify the printing path for the 3D printer nozzle which usually moves in straight lines.

Figure 6:
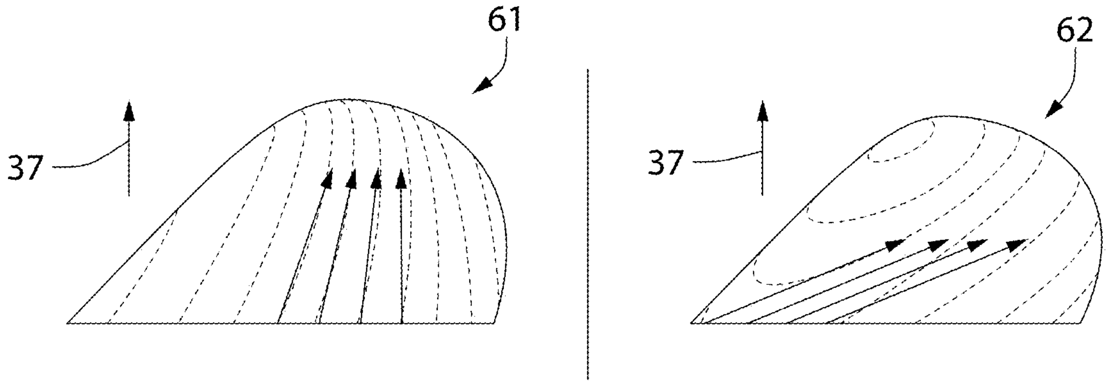
FIG. 6 shows two different implants according to various embodiments

In a further step of the method, the previous two steps (i.e. infilling the layers and forming printing paths) are performed with regard to one or more layers lying on those layers which have been processed so far (previously) and using a set of infill lines for that purpose which are arranged at an angle, preferably at 90°, to the set of infill lines that have been used for the layers processed so far (previously). The separation of the layers of a 3D object into two two batches of layers reflects the criss-cross nature of the printing process. It is noted that the criss-cross pattern is formed by repeatedly depositing one or more (a) infill lines in a first direction, then depositing one or more (b) infill lines in another direction, the other direction oriented at an angle, preferably 90°, to the first direction, and then by repeating the process at least one time, preferably multiple times. In that manner, by adjusting the number of layers in each batch, the height of the walls of the pores may be varied from one layer to the next. In the special case of a=b, the criss cross pattern is formed by an infill pattern of the 3D model, where every other infill line is oriented in the first direction, with single infill lines being arranged in between and oriented in the second direction being different from the first direction (see FIG. 7, for example). In the case of the second direction being 90° to the first direction, each channel has a square cross-section when viewed parallel to the print direction. For example, the first batch of layers may include layers of the 3D object having odd numbers, starting with the first layer (the bottom layer) of the 3D object. For the first batch of layers, the infill lines may be parallel to an x-axis of a coordinate system in which a 3D model of the 3D object to be printed is processes/represented. The second batch of layers may include layers of the 3D object having even numbers, starting with the layer second layer of the 3D object. In case of rectangular pores, the infill lines used for infill the layers of the second batch of layers may be parallel to a y-axis of the coordinate system in which a 3D model of the 3D object to be printed is processes/represented. In case of tapered channels, the distance between the infill lines grows smaller or larger from one layer to the next, starting at the bottom layer, depending on whether the channels are converging (as shown in FIGS. 4, 5 and 6, for example) or diverging.

According to further embodiments of the method, in case of constant channels (see FIG. 3, for example), the distance between the lines may be the same for all the layers.

According to further embodiments of the method, a first line of the set of lines used for a layer of one batch of layers may be laterally offset with respect to a first line of the set of lines used for an adjacent layer. This may also be the case for all the other lines in the sets used for adjacent layers. The position of the first infill line in a respective layer may correspond to the intersection line between a boundary plane of the 3D model and a plane in which the layer is embedded. The 3D model may be bound by three boundary planes, wherein one plane may correspond to the plane in which the bottom layer of the 3D model is embedded. The cross-sectional shape of the confining region of the 3D model may be triangular, e.g. when viewed in the xz-plane in the 3D model representation coordinate system.

According to further embodiments, the method may further include steps aiming at determining a confining region for the 3D model. Accordingly, the method may further include intersecting the representation of the 3D model of the porous object with a plane to form a working plane and performing subsequent steps in the working plane. The working plane, without loss of generality, may correspond to the xz-plane in the 3D model representation coordinate system, with the origin of the coordinate system being located at the projection of the center of mass of the 3D model on the bottom surface or at the center of the bottom layer of the 3D model, for example. The method may further include specifying a pore dimension of a first pore in a layer at a first height, preferably at a base (bottom surface) of the 3D model, represented by a first line segment (which lies in the working plane). The method may further include specifying a pore dimension of a second pore in a (different) layer of the porous object at a second height of the 3D model, represented by a second line segment (which also lies in the working plane), the first pore and the second pore belonging to the same channel. The pore dimensions of the first and second pores may correspond to the distances between the lines used for infill of the respective layers. The method may further include calculating a first orientation line by connecting left end points of the first and second line segments and calculating a second orientation line by connecting right end points of the first and second line segments. The method may further include calculating an intersection of the first and second orientation lines. That intersection corresponds to a point of convergence of walls associated with the respective pores in the case of non-constant channels, i.e. diverging or converging channels. The point of convergence lies above the xy-plane for converging channels or below the xy-plane for diverging channels, with the base or bottom layer of the 3D model being embedded in the xy-plane. The method may further comprise choosing a main orientation line which corresponds to that one of the first and second orientation lines which has a smaller distance to the center of the base of the 3D model or to the projection of the center of mass on the base of the 3D model. The method may further include varying the slope of the main orientation line to determine a first boundary line and a second boundary line, both running through the intersection (point of convergence) and being tangential to the 3D model. Both the first and the second boundary lines may each be expanded to a corresponding boundary plane (tangential plane) which is arranged at an angle, e.g. perpendicularly, to the xz-plane. Finally, the method may include confining the region in which intersections between the contour of a layer and the set of infill lines are determined to the region bound by the intersection between a plane comprising that respective layer and the first and second tangential planes.

Figure 8:
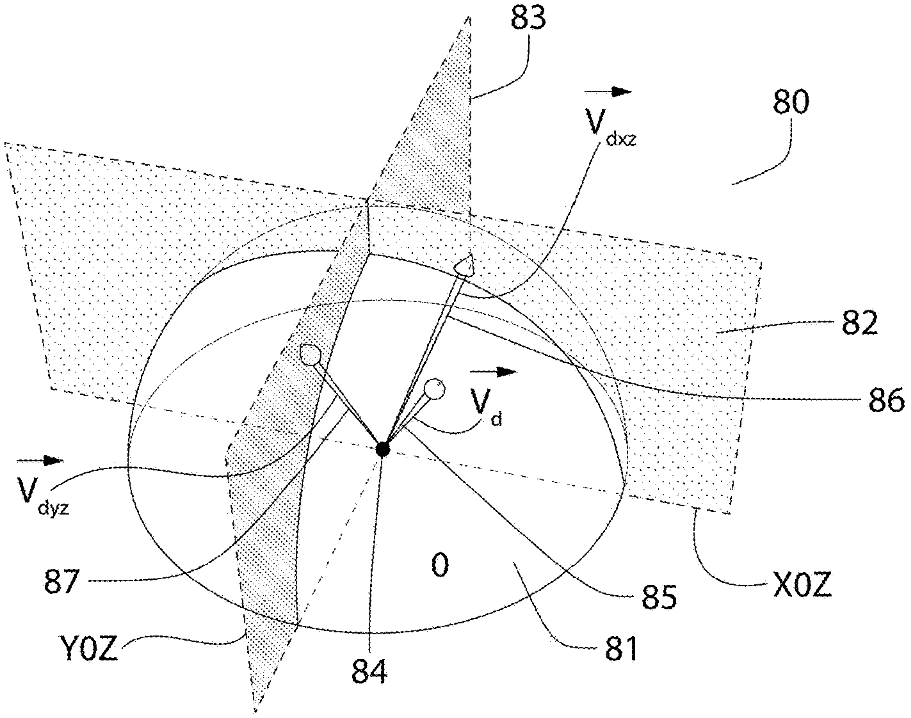
FIG. 8 shows a modeling space used for the calculation of the printing path according to a method of the invention.

In the following, an exemplary embodiment of the method will be described. In FIG. 8, a 3D model 81 is shown in a modeling space 80. In this example, the 3D object 81 is modeled by a hemisphere. In general, the 3D model 0={G} is composed of a set of geometrical functions G. The modeling space 80 comprises a 3D model representation coordinate system with its origin 84 located at the center of the bottom layer or at the point corresponding to the projection of the center of mass of the 3D object 81 on the base thereof. The base or bottom surface of the 3D model 81 lies in the xy-plane (defined by x- and y-axis of the coordinate system) which is not explicitly shown in FIG. 8. A direction vector $\overrightarrow{V_d}$(also carrying reference number 85) is shown which denotes the tilt/slant direction of the channels and is a parameter which may be provided by the user. Bottom-up assembly approaches by 3D printing mostly consider vertical and horizontal depositions along the x-axis and y-axis, respectively, in the xy-plane of the coordinate system.

Accordingly, the direction vector $\overrightarrow{V_d}$is projected onto the xz-plane 82 (defined by x- and z-axis of the coordinate system) and onto the yz-plane 83 (defined by y- and z-axis of the coordinate system) of the coordinate system such that two resulting direction vectors $\overrightarrow{V_{d_{xz}}}$(also carrying reference number 86) and $\overrightarrow{V_{d_{yz}}}$(also carrying reference number 87) are the projected direction vectors of channels for vertical and horizontal deposition, respectively. The following description will focus on the manufacturing of layers in which the inner scaffold comprises strands of print material extruded parallel to the y-axis. The same procedure can be used for the planes which comprise paths of extruded material arranged along the x-axis.

In addition to the user defined geometric information {G} with regard to the outer shape of the 3D model 81channel direction vector $\overrightarrow{V_d}$, the present method may receive the following input parameters from a user:

- $D_n$: diameter of the nozzle of the 3D printer,
- LT: layer thickness, i.e. thickness of the strands of the material deposited by the nozzle, with the boundary condition $LT<D_n$,
- $Pore_b$: pore size at the base of the 3D model 81,
- $Pore_u$: pore size at a user defined height $h_u$,
- $h_u$: user defined height at which the pore size $Pore_u$ is specified.

Figure 9A:
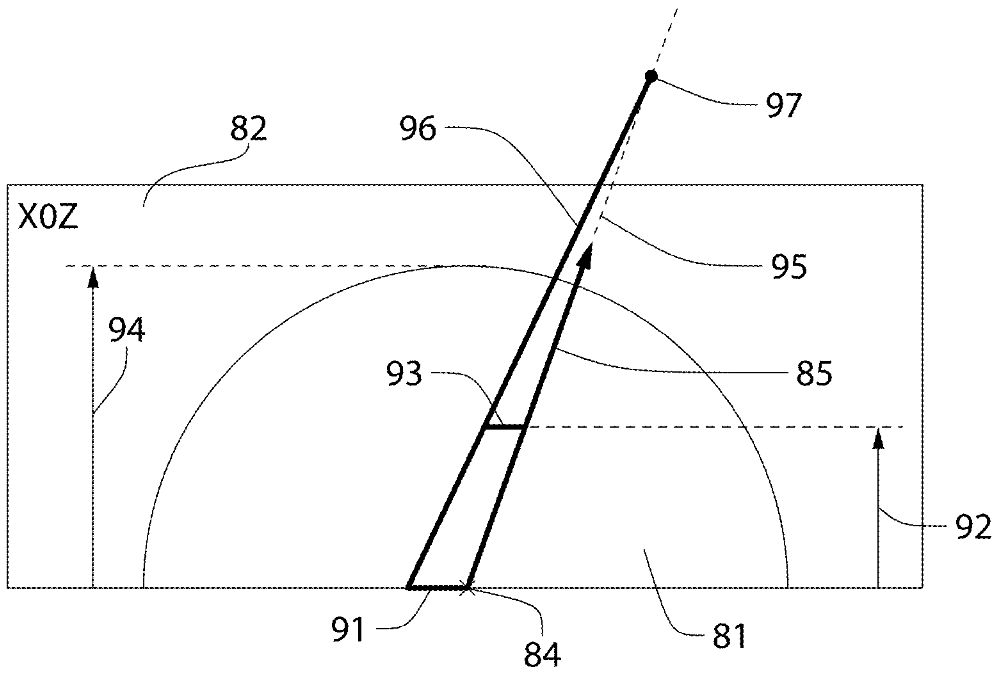
FIGS. 9A and 9B illustrate the calculation of concentration points of the channels of the 3D model.
Figure 9B:
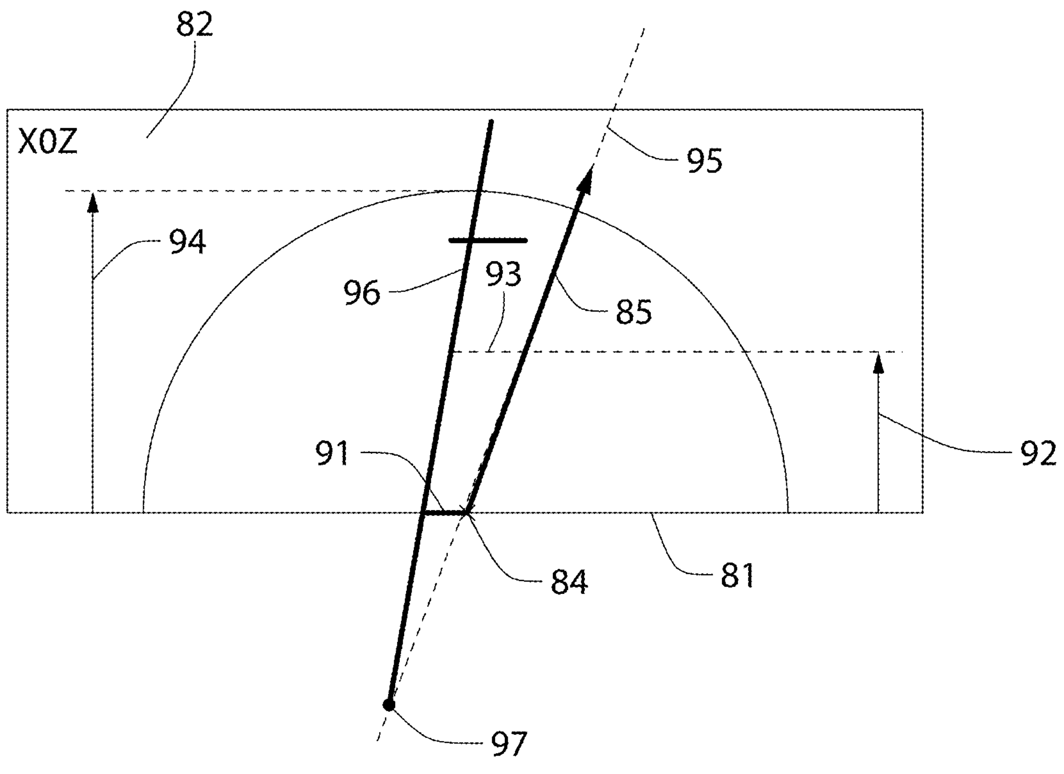

At least a subset of the user defined parameters may be used to calculate the point of convergence of walls which define the channels of the 3D model 81. This will be explained on the basis of FIGS. 9A and 9B which show the scenario for converging channels and for diverging channels, respectively, in the xz-plane of the coordinate system from FIG. 8A. Based on the input data, an algorithm is used to determine whether the channels are convergent or divergent. Pores is represented by a first line segment 91, wherein one of the end points thereof corresponds to the origin 84 of the coordinate system. $Pore_u$ is represented by a second line segment 93 at the user defined height 92. The overall height of the 3D model 81 corresponds to the second height 94. $Pore_b$ and $Pore_u$ may relate to the same channel of the 3D model 81, wherein the position of the second line segment 93 with respect to the first line segment 91 in the xz-plane 82 can be derived from the direction vector 85. In general, a linear correlation exists between pore size $Pore_u$ and height $h^u$ of the corresponding pore. The point of convergence 97 of the channels (or the walls thereof) is determined by calculating a first orientation line 96 by connecting left end points of the first line segment 91 and the second line segment 93 and calculating a second orientation line 95 by connecting right end points of the first line segment 91 and the second line segment 93. As shown in FIGS. 9A and 9B, the direction vector 85 lies on the second orientation line 95. The first and second orientation lines 96, 95 correspond to one-dimensional representations of the walls of a channel. By calculating the intersection of the first and second orientation lines 96, 95, the point of convergence 97 of the walls is obtained. Depending on the location of the point of convergence 97 with respect to the 3D model 81, i.e. whether the point of convergence 97 lies above the 3D model 81 and therefore above the xy-plane, as shown in FIG. 9A, or below the 3D model 81 and therefore below the xy-plane, as shown in FIG. 9B, the algorithm may determine whether the channels are converging or diverging. It is noted that in the case of constant channels, the first and second line segments 96, 95 are parallel and the direction vector 85 corresponds to the second arrow 38 which denotes the orientation of the constant channels (see FIG. 3).

Figure 10:
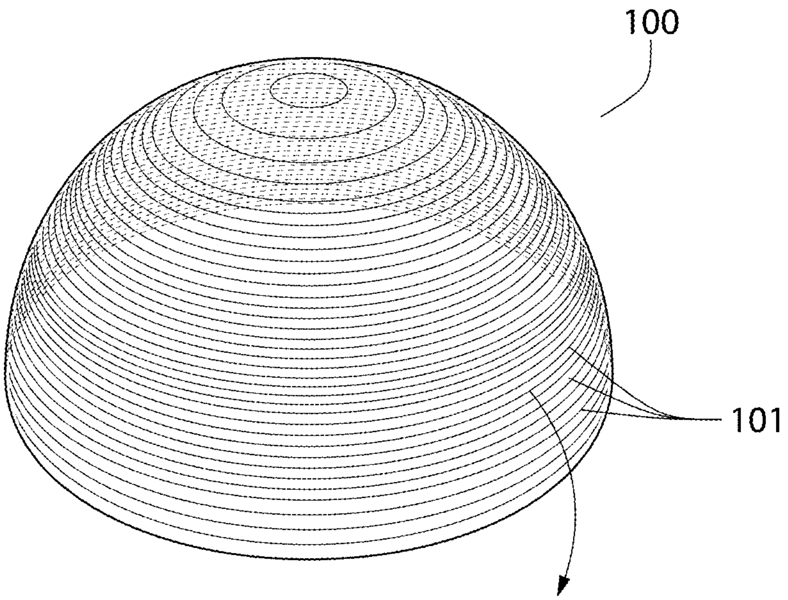
FIG. 10 illustrates the segmentation of the 3D model into layers.

After the nature of the channels has been determined, the 3D model 81 of the porous object shown in FIG. 10 is decomposed into a set of layers 101, each layer comprising a contour of the 3D model at a respective height of the 3D model. In the example of a 3D model 81 in the form of a hemisphere, each layer 101 corresponds to a disk arranged parallel to the xy-plane of the coordinate system and can be extruded during printing by purely two-dimensional movement of the nozzle.

Figure 11:
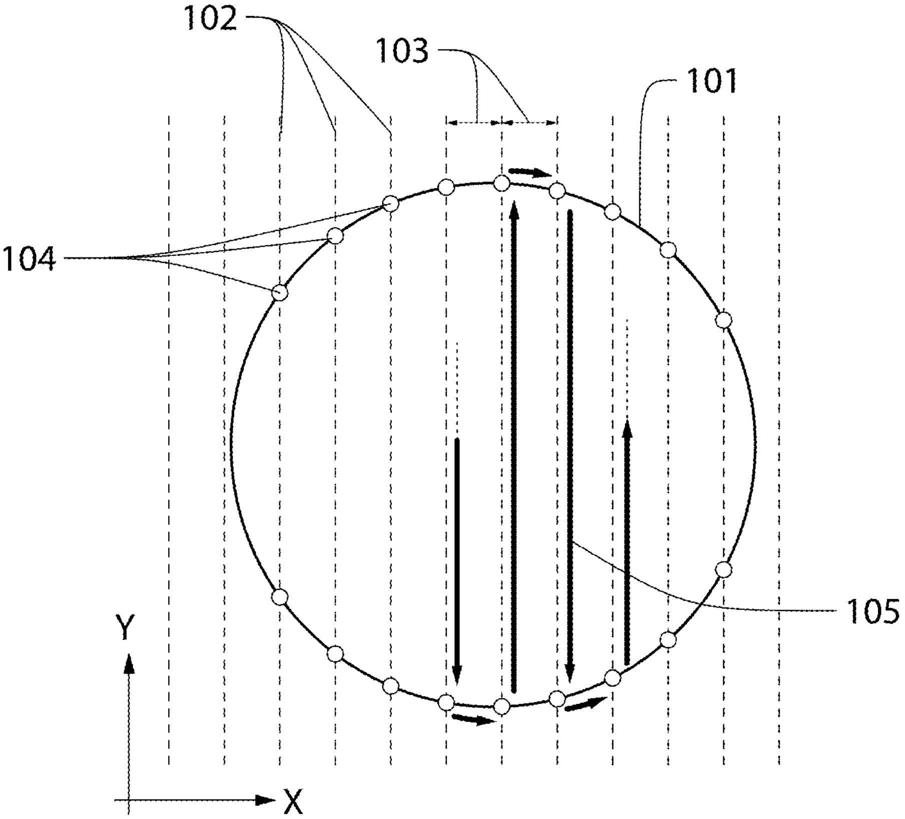
FIG. 11 illustrates the infill of a layer of the 3D model.

In the next step illustrated in FIG. 11, a printing path is determined for each layer 101. This is done by intersecting each layer 101 with a set of infill lines 102, wherein the distance 103 between the infill lines 102 for each layer 101 is set to correspond to the dimension of the pores in that layer 101 in a direction perpendicular to the infill lines. For example, for a layer at the user defined height $h^u$ (see FIGS. 9A and 9B), the distance 103 between the infill lines 102 would correspond to the pore size $\text{Pore}_u$. The printing path is determined on the basis of the intersections 104 between the set of infill lines 102 and the contour of the layer 101. A section of the printing path 105 is indicated in FIG. 11. The printing path is formed by an ordered set of the intersections 104, wherein the intersections 104 are arranged as indicated by the arrows forming the printing path 105 (i.e. lower intersection 104 of n-th infill line→upper intersection 104 of nth-infill line→upper intersection 104 of (n+1) th infill line→lower intersection 104 of (n+1) th infill line).

In more detail, the 3D object 81 is presented as set of S layers 101, $\{L^s\}_{s=1, \ldots, S}$, and each layer $L^s$ at the respective height of $h_s$ contains geometrical information G, primarily the form of the contour of the layer (circular, oval, etc). Each layer $L^s$ can be defined as a set of contours, $$L^s = \{CO_q^s\},\ q = 1, \ldots, Q$$

Each contour $$CO_q^s$$

is a closed curve which represents the external boundaries of the 3D model 81 at the level of the respective layer $L^s$. The deposition of print material over layer s is represented by the preferably parallel infill lines $$\{l_a^s\},\ a = 1, \ldots, A.$$

As already mentioned, the distance between the infill lines $$l_a^s$$

is set to correspond to the size of the pores of a respective layer at the corresponding height $h_s$. The starting position of the first line $$l_1^s$$

may be defined by the intersection line of a tangential plane with a plane in which the respective layer is embedded. This aspect will be explained in more detail later on. An ordered set of points $$\{P_t^s\},\ t = 1, \ldots, T$$

is generated for path planning of the 3D printing by arranging the intersections 104 in an ordered manner, as already explained. These points $$P_t^s$$

form the printing path which the nozzle of the 3D printer follows during 3D printing.

In case of non-constant channels, i.e. convergent or divergent channels, the size of pores changes gradually from one layer to the next. At the same time, the number of pores is equal for all the layers $L^s$, also in the case of constant channels.

Figure 12A:
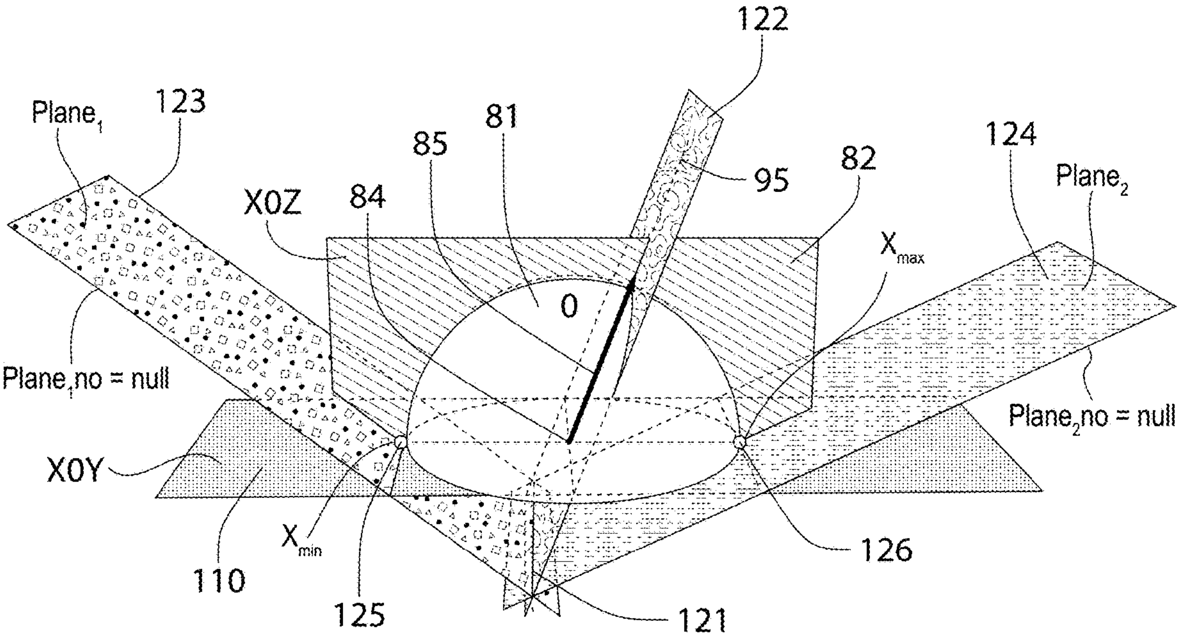
FIGS. 12A and 12B illustrate the calculation of a bounding region of the 3D model.
Figure 12B:
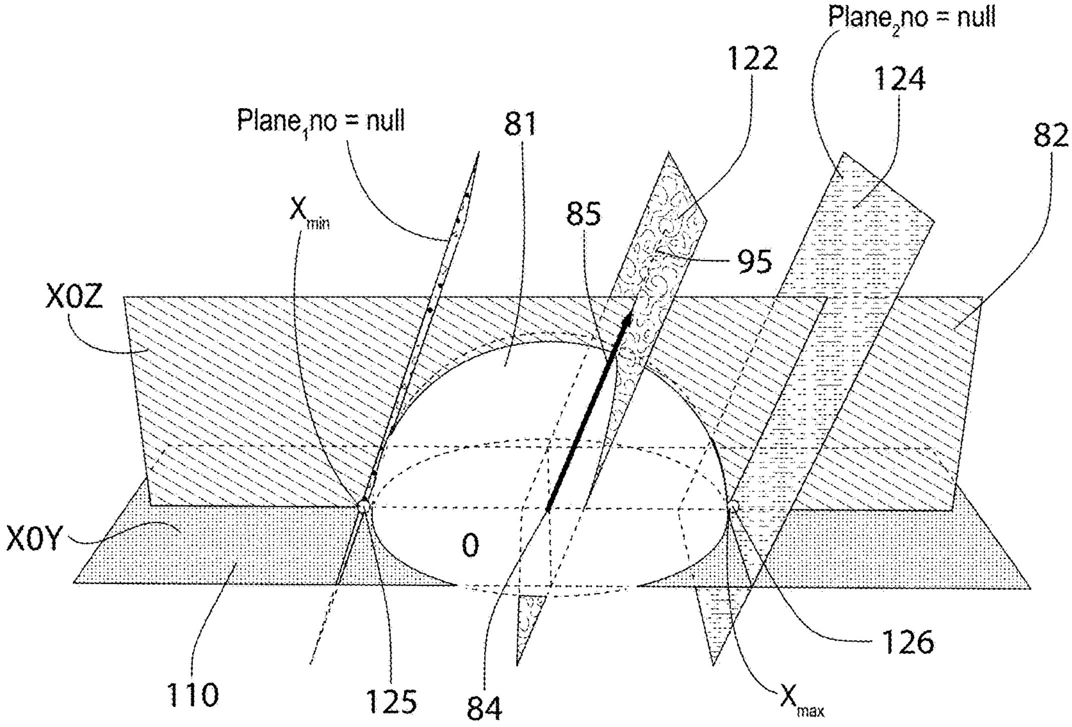

The number of infill lines 102 should be as small as possible in order to reduce the required computational time. In order to do so, the relevant region in which the infill lines 102 are arranged can be restricted, e.g. by calculation of two bounding planes. The calculation of the bounding planes is explained in FIGS. 12A and 12B, wherein FIG. 12A illustrates the scenario for divergent channels and FIG. 12B illustrates the scenario for constant channels. The calculation is based on the representation of the 3D model 81 shown in FIG. 8. First, an axis of rotation 121 is calculated by expanding the point of point of convergence 97 into a line which is parallel to or preferably in the xy-plane 120. In an analogous manner, a direction plane 122 may be formed based on the direction vector 85, wherein the direction plane 122 is perpendicular to the xz-plane 82. By varying the slope of the second orientation line 95 (i.e. extension of the direction vector 85) while keeping the second orientation line 95 anchored at the point of convergence 97, a first boundary line having a negative slope and a second boundary line having a positive slope, both being tangential to the 3D model 81, may be determined. The tilting/rotating of the second orientation line 95 about the point of convergence 97 corresponds to tilting/rotating of the direction plane 122 about the axis of rotation 121. A corresponding first bounding plane 123 and second bounding plane 124 may be determined by expanding the first boundary line and the second boundary line into planes perpendicular to the xz-plane 82. Both bounding planes 123, 124 are tangential to the 3D model 81. The bounding planes 123, 124 are then used to limit the region in which the intersections 104 are determined. That region may be bound by the intersection lines between a plane comprising that respective layer 101 and the first and second tangential planes 123, 124. Either of those intersection lines may be used as the first infill line $$l_1^s$$

for a given plane 101. The first infill lines $$l_1^s$$

for the other layers 101 may correspond to the intersection lines between the plane of the respective layer 101 and the same one of the first and second tangential bounding planes 123, 124. The intersection lines for the bottom layer of the 3D model 81 are shown in FIG. 12A as lines which are perpendicular to the xz-plane 82 and which are running through a first bounding point 125 ($X_{min}$) and a second bounding point 126 ($X_{max}$). The first bounding point 125 and the second bounding point 126 correspond to intersections between the xy-plane 120 and the first and second boundary lines.

The scenario for convergent channels is analogous to the one shown in FIG. 12A and mainly differs therefrom in that the axis of rotation 121 is not arranged below the xy-plane 120, but above the xy-plane 120. Accordingly, the slopes of the first and second bounding planes 123, 124 are inverted, i.e. the slope of the first bounding plane 123 is positive and the slope of the second bounding plane 124 is negative. In the case of constant channels, where accordingly a point of concentration 97 does not exist since the direction vector 85 describing the orientation of the channels, the first boundary line and the second boundary line are parallel, the first boundary line and the second boundary line (and the corresponding first and second bounding planes 123, 124) are obtained by a translation of the second orientation line 95 until it becomes tangential to the 3D model 81.

The pore size Pores at any s-th layer 101 can be defined by first calculating the number of pores N in the first layer (bottom layer):

$$N = (X_{max} - X_{min})/\text{Pore}_b$$

Then, by using the calculated number of pores N, which for reasons of consistency remains constant for all the layers of the 3D model, the pore size Pores at the s-th layer can be determined:

$$\text{Pore}_s = (X_{max} - X_{min})^s/N$$

Figure 13A:
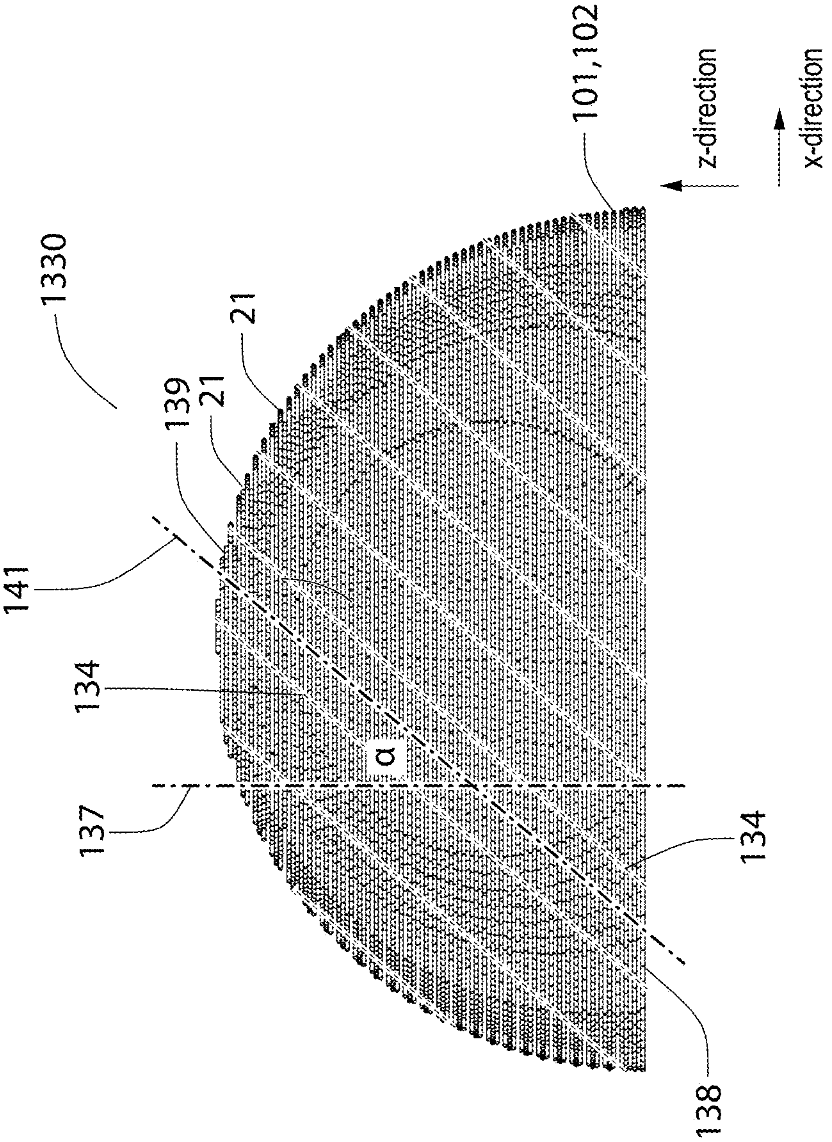
FIG. 13A shows a cross-sectional side view of an implant according to various embodiments.

FIG. 13A shows a cross-sectional side view of an implant 1330 for insertion into a patient according to various embodiments.

The implant 1330 comprises a three dimensionally (3D) printed structure of layers 101. Each layer 101 comprises an infill pattern (as described in connection with FIG. 7) of the three-dimensionally printed structure. The infill pattern of each layer comprises a set of infill lines 102. The implant 1330 further comprises a plurality of hollow channels 21. The layers 101 are arranged on top of one another such that the plurality of hollow channels 21 are formed within the implant 1330. The walls 134 of each channel 21 are formed by sections of the infill lines of a plurality of layers of the printed structure of layers. At least one hollow channel (21) extends between a first outer surface 138 of the implant and a second outer surface 139 of the implant. The at least one hollow channel (21) is oriented in a direction (53) which is tilted with respect to a reference axis 137 perpendicular to the first outer surface of the implant.

The first outer surface 138 of the implant may be the largest planar (flat) surface of the implant. For example, the first outer surface 138 may be a flattest surface of the implant and/or surface with the least amount of curvature. The first outer surface 138 may be the bottom surface, which may be the surface of the implant facing, or closest to the chest-wall of the patient after insertion into the patient. The first outer surface of the implant may be parallel to a two-dimensional (x-y) plane formed by a first layer (or one or more layers) of the three-dimensional (3D) printed structure. The cross-sectional side view of FIG. 13A may be from a cross-section perpendicular to the first outer surface 138, i.e. perpendicular to the x-y plane.

Additionally, or optionally, the second outer surface 139 may be a non-coincident (e.g. non-intersecting) surface to the first outer surface 138. The second outer surface 139 may be a side surface of the implant, or a top surface of the implant. Optionally, the first outer surface 138 of the implant and the second outer surface 139 may be opposite-facing surfaces. For example, the first outer surface of the implant may be a bottom surface, and the second outer surface may be a top surface. Optionally, the second outer surface 139 may be a curved surface of the implant. A channel 21 (or a projection, or extension of the channel 21) may terminate at the second outer surface 139, defining a point of intersection between the channel 21 and the second outer surface 139. A tangential plane at the point of intersection between the channel 21 and the second outer surface 139 may be non-parallel to the x-y plane.

The tilt-to-reference angle, a, may be defined as the angle between the reference axis 137 and the central longitudinal axis 141 of a channel 21. The reference axis 137 may be perpendicular to the x-y planes of the layers (e.g. perpendicular to majority of the layers, e.g. perpendicular to more than 50% of the layers). For example, the reference axis 137 may be parallel to the z-axis. For example, the reference axis 137 may be perpendicular to a plane formed by the first outer surface 138 of the implant. The tilt-to-reference angle, a, may lie between 10 degrees and 85 degrees (or e.g. between 45 degrees and 85 degrees), in the cross-sectional side view of the implant 1330, the cross-sectional side view being perpendicular to the x-y plane.

The central longitudinal axis 141 of a channel 21 may be a central longitudinal axis of symmetry which may be a straight line lying at the mid-points of the infill-lines forming the walls 134 of the channel 21. Optionally, in the case of non-tapered channels, the central longitudinal axis 141 may be parallel to each of the walls 134 of the channel 21.

At least one hollow channel 21 (e.g. one or more hollow channels 21) extends between a first outer surface 138 of the implant and a second outer surface 139 of the implant. Optionally, more than 30% (or e.g. more than 50%, or e.g. more than 80%, or e.g. each) of the hollow channels 21 extends between the first outer surface 138 and the second outer surface 139. "Extending between the first outer surface 138 and the second outer surface 139" may be understood to include examples even if the channels 21 do not terminate directly at the surfaces. For example, "extending between the first outer surface 138 and the second outer surface 139" may include examples wherein the channels 21 terminate (one or more layers) before reaching the first outer surface 138 and the second outer surface 139, in other words, where the openings of the channels 21 are not necessarily formed at the outer-most layers of the implant. In some examples, it may be possible that the channel 21 includes a slanted (tilted) portion and at least one non-tilted portion. A non-tilted portion of the channel 21 may be a portion which is parallel to the reference axis (e.g. the tilt-to-reference angle is zero). For example, a (first) non-tilted portion may have an opening at the first outer surface of the implant. The tilted portion of the channel 21 may be located between the first non-tilted portion and optionally a second non-tilted portion having an opening at the second outer surface of the implant. A non-tilted portion of the channel 21 may be formed from one or more (e.g. a plurality) of the outer-most layers of the implant at the first outer surface of the implant or the second outer surface of the implant.

"Extending between the first outer surface 138 and the second outer surface 139" may also include examples, wherein at least one end of the channel terminates at an outermost layer of the implant. For example, a channel 21 may extend completely from the first outer surface 138 to the second outer surface 139. For example, the channel 21 originates at the first outer surface 138 and terminates at the second outer surface 139. It may further be understood that it is possible that not all the hollow channels 21 originate from the first outer surface 138 and terminate at the second outer surface 139. For example, it is possible that some of the channels 21 (or extrapolations of the channels) at the side of the implant do not originate at the first outer surface 138.

At least 10% (or e.g. at least 20%, or e.g. at least 30%, or e.g. at least 50%, or e.g. all) of the hollow channels of the plurality of hollow channels may be tilted with respect to the reference axis by the same tilt-to-reference angle. Hollow channels having the same tilt-to reference angle may be aligned in the same direction, and the magnitude of the tilt-to-reference angle may be the same. Alternatively or optionally, more than two hollow channels (or e.g. more than 3 hollow channels, or more than 5 hollow channels) of the plurality of hollow channels may be tilted with respect to the reference axis by the same tilt-to-reference angle. In the case of the tilted constant channels, the tilt-to-reference angle may be the same for each of the channels. In other words, all the hollow channels of the implant may be parallel to each other, ignoring deviations due to manufacturing imperfections.

Optionally, at least one hollow channel (or e.g. one or more or all of the hollow channels) may be a tapered channel. Optionally, the plurality of hollow channels may converge towards a predefined region at the first outer surface or at the second outer surface of the implant. In some embodiments, the predefined region may be point of convergence located directly on the first outer surface or directly on the second outer surface of the implant. Alternatively, the predefined region may be a point of a convergence located beyond (outside) the first outer surface or beyond (outside) the second outer surface of the implant. In other words, the point of convergence may be located outside the implant (as described in connection with FIGS. 9A and 9B).

Figure 13B:
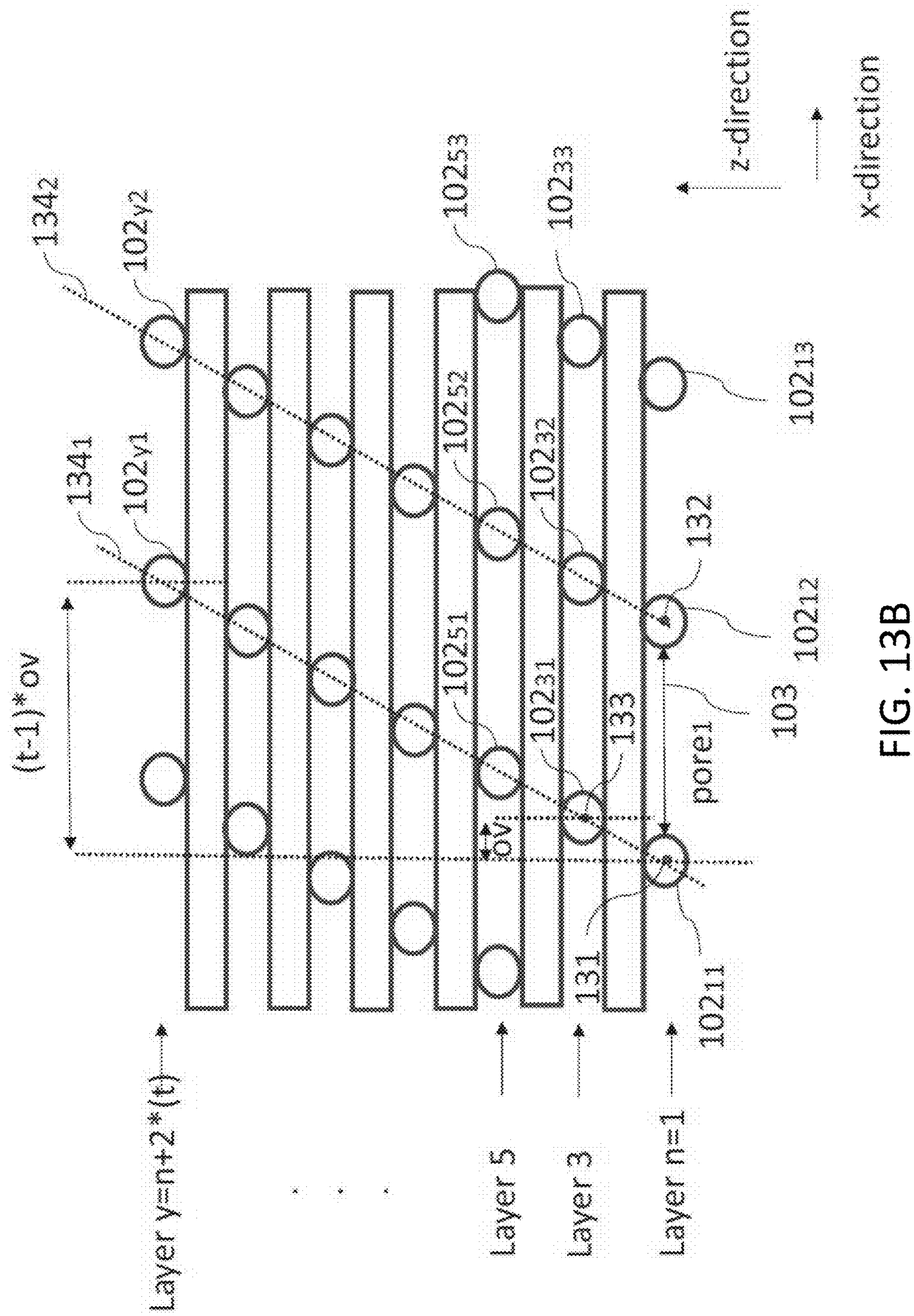
FIG. 13B shows a cross-sectional side view of an implant comprising tilted/slanted hollow channels according to various embodiments.

FIG. 13B shows a cross-sectional side view illustration of the implant 1330 comprising tilted/slanted hollow channels according to various embodiments.

The three-dimensionally (3D) printed structure of layers may include a first batch of layers and a second batch of layers. The first batch of layers may include odd-numbered layers of the three-dimensionally (3D) printed structure of layers, and the second batch of layers may include even-numbered layers of the three-dimensionally (3D) printed structure of layers.

The infill lines of the first batch of layers may be oriented in a first direction, and the infill lines of the second batch of layers may be oriented in a second direction different to the first direction. Portions of the infill pattern of the odd-numbered layer of the first batch of layers may be shifted with respect to portions of the infill pattern of a first infill layer of the first batch of layers. Additionally, or optionally, portions of the infill pattern of the even-numbered layers of the second batch of layers may be shifted with respect to portions of the infill pattern of a first infill layer of the second batch of layers.

Each odd-numbered layer of the plurality of layers of the 3D printed structure may include a first infill line $\mathbf{102}_{y1}$ and a second infill line $\mathbf{102}_{y2}$ which may be parallel to and directly adjacent to the first infill line $\mathbf{102}_{y1}$ of the odd-numbered layer. By way of example, the odd-numbered layers may refer to layer 1, layer 3, layer 5 and so on, or generally by the formula layer n+2*(t), where t is an integer greater than or equal to 0. t may be, but is not limited to being, an integer which lines between 30 and 200, for example. As shown in FIG. 13A, an arbitrary first odd-numbered layer (layer 1) may be a layer, where n=1, and t=0. The first odd-numbered layer may be, but is not limited to being the outermost layer at the first outer surface of the implant.

A lateral pore dimension ($pore_1$) may be a distance 103 between a first infill line $\mathbf{102}_{11}$ of the first odd numbered-layer (layer 1) and a second adjacent (directly subsequent) infill line $\mathbf{102}_{12}$ of the first odd-numbered layer. The distance 103 may be measured in a direction (x-direction) perpendicular to a central longitudinal axis 131 of the first infill line $\mathbf{102}_{11}$ of the first odd-numbered layer and/or to the central longitudinal axis 132 of the second infill line $\mathbf{102}_{12}$ of the first odd-numbered layer. The central longitudinal axis 131 of the first infill line $\mathbf{102}_{11}$ of the first odd-numbered layer may be an axis parallel to the length of the first infill line $\mathbf{102}_{11}$ (e.g. parallel to the y-axis) of the first odd-numbered layer. The central longitudinal axis 132 of the second infill line $\mathbf{102}_{12}$ of the first odd-numbered layer may be an axis parallel to the length of the second infill line $\mathbf{102}_{12}$ of the first odd-numbered layer.

A lateral offset value, ov, may be defined as the smallest distance between the central longitudinal axis 131 of a first infill line of the first odd-numbered layer and a central longitudinal axis 133 of a first infill line $\mathbf{102}_{31}$ of the second odd-numbered layer (e.g. layer n+2=3). The central longitudinal axis 133 of the first infill line $\mathbf{102}_{31}$ of the second odd-numbered layer may be an axis parallel to the length of the first infill line $\mathbf{102}_{31}$ (e.g. parallel to the y axis) of the second odd-numbered layer. The lateral offset value, ov, may be a dimension measured in a horizontal direction, parallel to the layer (e.g. parallel to the x-axis).

The lateral offset value, ov, may be larger than zero and less than 50% (or e.g. less than 30%, or e.g. less than 10%, or e.g. less than 5%, or e.g. less than 1%) of the pore size, 103 (or $pore_1$), of the first pore of the first layer (layer 1), ignoring deviations due to manufacturing imperfections.

The infill lines 102 of the plurality of odd-numbered layer of the channel 21 may be arranged, so that the portion of an infill line $\mathbf{102}_{11}$ of an odd-numbered layer (e.g. layer 1) forming part of the wall $\mathbf{134}_1$ of the hollow channel 21, may be offset with respect to the nearest (or closest), parallel infill line $\mathbf{102}_{31}$ of the adjacent odd-numbered layer (e.g. layer 3) forming part of the same wall $\mathbf{134}_1$ of the same hollow channel 21 by the lateral offset value, ov. By way of example, a portion of an infill line of the n+2*(1) layer may be offset with respect to the nearest (or closest), parallel infill line of the n layer by the lateral offset value, ov. A subsequent odd-numbered layer, n+2*(2) may be offset with respect to the nearest parallel infill line of the n+2*(1) layer by the same lateral offset value. In the case of constant channels, the lateral offset value may be constant (or the same) for more than 80% of the layers of the implant, ignoring deviations due to manufacturing.

All the portions of the infill lines forming the same wall of the same hollow channel may have an accumulative (summative) lateral offset value with respect to the infill line of the first layer forming that wall. In the case of constant tilted channels, the accumulative lateral offset value may be a multiple of the lateral offset value between the directly subsequent odd numbered layers. For example, the first infill line of the n+2*(t) layer of the wall $134_1$ may have an accumulative lateral offset value of ((t−1)*ov) with respect to the first infill line $102_{11}$ of the first layer of the wall $134_1$. The infill lines may be arranged so that the accumulative lateral offset value of ((t−1)*ov) may be larger than or equal to the pore size, 103 (or $pore_1$) of the first pore of the first layer only for integer values of t larger than 2 i.e. for odd-numbered layers 7, 9 and onwards. In this case, t may be, but is not limited to values, such as 2<t<8, or e.g. 4<t<20. In other words, for values of t smaller than or equal to 2, the accumulative lateral offset value ((t−1)*ov) may be less than the pore size, 103 (or $pore_1$), ignoring deviations due to manufacturing. Alternatively or optionally, in the case where the tilt-to reference angle is very small (e.g. less than 5 degrees), the accumulative lateral offset value of ((t−1)*ov) may be smaller than the pore size, 103, even for integer values of t larger than 2.

The wall $134_1$ of a slanted channel 21 extending between the top surface of the implant and the bottom surface of the implant may be comprised of portions of the infill lines 102 from every odd-numbered layer. The wall $134_1$ may be formed by the infill lines of a plurality of odd-numbered layer of the channel 21, so that a portion of an infill line $102_{11}$ of an odd-numbered layer (e.g. layer 1) and a portion of a nearest (closest) parallel infill line $102_{31}$ of an adjacent (or directly subsequent) odd-numbered layer (e.g. layer 3) form part of the same wall $134_1$ of the same hollow channel 21. Similarly, a portion of a parallel infill line $102_{51}$ of an adjacent (or directly subsequent) odd-numbered layer (e.g. layer 5) forms part of the same wall $134_1$ of the same hollow channel 21.

Any of the walls of a hollow channel may be formed by a section of every other layer in the arrangement of layers forming the implant. A first wall $134_1$ of a hollow channel 21 may be formed from a portion of the first infill lines of the odd-numbered layers. A second wall $134_2$ of the hollow channel 21 may be formed from a portion of the second infill lines of the odd-numbered layers. The second wall $134_2$ may also be a wall of a second neighbouring (directly adjacent) hollow channel, which in the case of tilted constant channels, may be parallel to the first hollow channel.

Each even-numbered layer (e.g. layers 2, 4, 6 . . . 2*t) of the plurality of layers of the 3D printed structure may include a first infill line and a second infill line which may be parallel to and directly adjacent to the first infill line of the even-numbered layer. A third wall of the hollow channel 21 may be formed from a portion of the first infill lines of the even-numbered layers. A fourth wall of the hollow channel 21 may be formed from a portion of the second infill lines of the even-numbered layers of the plurality of layers.

In some other examples, a lateral offset value between a first infill line $102_{11}$ of a first odd-numbered layer and a first infill line $102_{31}$ of a second odd-numbered layer lies between 50% and 100% (e.g. between 55% and 95%) of a distance between the first infill line $102_{11}$ of the first odd-numbered layer and a second adjacent infill line $102_{12}$ of the first odd-numbered layer. An accumulative lateral offset value between a first infill line $102_{11}$ of an odd-numbered layer (e.g. an n+2*t layer) and the first infill line $102_{11}$ of the first odd-numbered layer may be larger than the distance between the first infill line $102_{11}$ of the first odd-numbered layer and the second adjacent infill line $102_{12}$ of the first odd-numbered layer, for values of t larger than or equal to 2.

It may be understood that the terms "odd-numbered layer" and "even-numbered layer" may refer to a single (i.e. one) layer, or it may also refer respectively to "odd-numbered sets of layers" and "even-numbered sets of layers". In other words, the term "odd-numbered layer" may refer to one or more layers within the odd-numbered set of layers. Likewise, the term "even-numbered layer" may refer to one or more layers within the even-numbered set of layers.

It may be understood that the features of the implant (the 3D printed structure of layers, the infill pattern, the infill lines, the plurality of hollow channels, the walls of the channels, the odd-numbered layers, the even-numbered layers) described in connection with embodiments of FIGS. 1 to 12B may also apply to the implant of FIGS. 13A and 13B.

Figure 13C:
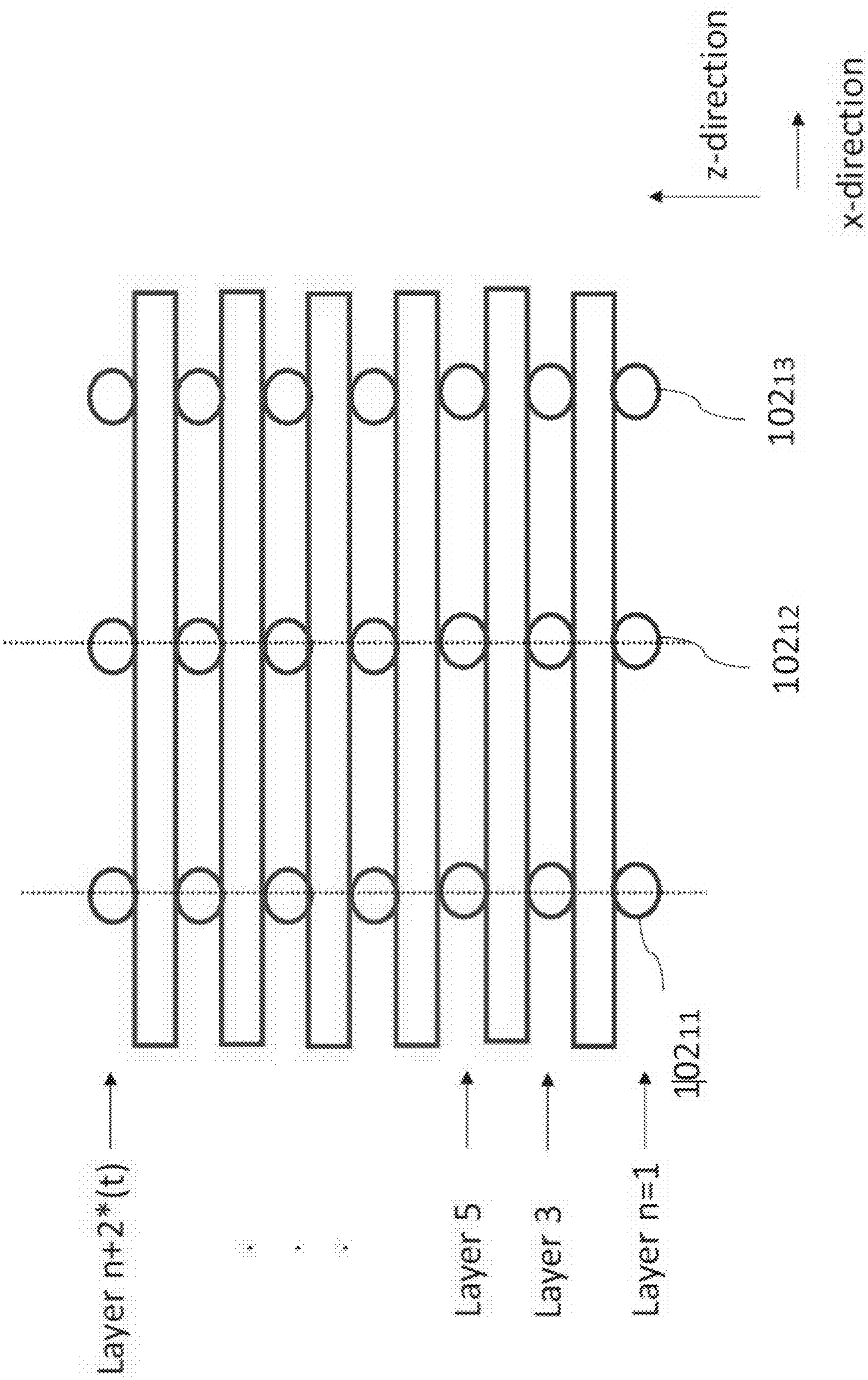
FIG. 13C shows an implant comprising non-tilted/non-slanted channels.

FIG. 13C shows an example of channels which are not tilted with respect to the print direction. As shown in FIG. 13C, the lateral offset value is zero.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, and specific compounds described herein are presently representative of certain embodiments are thus exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied herein may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of tissue reconstruction or tissue augmentation, the method comprising implanting into the body of a subject an implant, wherein the implant comprises:

a three-dimensionally (3D) printed structure of layers, wherein each layer comprises an infill pattern of the three-dimensionally printed structure, the infill pattern of each layer comprising a set of infill lines, wherein the layers are arranged on top of one another such that a plurality of adjacent tilted hollow channels comprising walls are formed within the implant;

wherein the adjacent tilted hollow channels are separated from one another by the walls, wherein a wall of a first tilted hollow channel is a wall of a second adjacent tilted hollow channel; and wherein each tilted hollow channel comprises slanted walls, wherein a slanted wall is formed by sections of the infill lines of a plurality of alternate layers of the printed structure of layers, wherein the sections of infill lines are oriented in a first direction, and arranged above one another with a lateral offset, wherein the lateral offset is a dimension in a direction parallel to a first outer surface of the implant, wherein the lateral offset is larger than zero and less than 50% of a lateral channel dimension, wherein the plurality of tilted hollow channels extends between a first outer surface of the implant and a second outer surface of the implant, wherein a tilted hollow channel is oriented in a direction which is tilted with respect to a reference axis perpendicular to the first outer surface of the implant.

2. The method of claim 1, wherein the method further comprises injecting fat into the implant.

3. The method of claim 2, wherein the implant is a breast implant.

4. The method of claim 3, wherein the method further comprises injecting fat into the breast implant.

5. The method of claim 4, wherein the fat is injected from under the breast fold (inframammary injection).

6. The method of claim 2, wherein the implant is inserted into the body and the fat is injected into the implant via the same incision.

7. The method of claim 1, wherein the first outer surface of the implant and the second outer surface are opposite-facing surfaces.

8. The method of claim 1, wherein the first outer surface is parallel to a two-dimensional plane formed by a first layer of the three-dimensional (3D) printed structure.

9. The method of claim 1, wherein the first outer surface is the largest planar surface of the implant.

10. The method of claim 1, wherein an angle between a longitudinal axis of a channel and the reference axis lies between 10 degrees and 85 degrees.

11. The method of claim 10, wherein the three-dimensionally (3D) printed structure of layers comprises a first batch of layers and a second batch of layers, wherein the first batch of layers comprises odd-numbered layers of the three-dimensionally (3D) printed structure of layers, and wherein the second batch of layers comprises even-numbered layers of the three-dimensionally (3D) printed structure of layers, wherein the infill lines of the first batch of layers are oriented in a first direction, and wherein the infill lines of the second batch of layers are oriented in a second direction different to the first direction, wherein portions of the infill pattern of the odd-numbered layer of the first batch of layers are shifted with respect to portions of the infill pattern of a first infill layer of the first batch of layers.

12. The method of claim 11, wherein portions of the infill pattern of the even-numbered layers of the second batch of layers are shifted with respect to portions of the infill pattern of a first infill layer of the second batch of layers.

13. The method of claim 12, wherein a lateral offset value between a first infill line of a first odd-numbered layer and a first infill line of a second odd-numbered layer lies between 0% and 50% of a distance between the first infill line of the first odd-numbered layer and a second adjacent infill line of the first odd-numbered layer.

14. The method of claim 12, wherein a lateral offset value between a first infill line of a first odd-numbered layer and a first infill line of a second odd-numbered layer lies between 50% and 100% of a distance between the first infill line of the first odd-numbered layer and a second adjacent infill line of the first odd-numbered layer.

15. The method of claim 12, wherein the plurality of hollow channels converges towards a predefined region at the first outer surface or at the second outer surface of the implant.

16. The method of claim 15, wherein the predefined region is a point of a convergence located beyond the first outer surface or beyond the second outer surface of the implant.

* * * * *